(12) United States Patent
Al-Uzri et al.

(10) Patent No.: US 10,939,861 B2
(45) Date of Patent: Mar. 9, 2021

(54) DRIED BLOOD SPOT COLLECTION DEVICE

(71) Applicants: Oregon Health & Science University, Portland, OR (US); Simplexity Product Development Inc., Vancouver, WA (US)

(72) Inventors: Amira Al-Uzri, Portland, OR (US); Dennis Koop, Beaverton, OR (US); Lisa Bleyle, Beaverton, OR (US); Andrew Chitty, West Linn, OR (US); Robert W. Beauchamp, Sant Cugat des Valles (ES); Asa Weiss, Portland, OR (US); Ethan Vella, Portland, OR (US); Gerold Firl, Poway, CA (US)

(73) Assignees: Simplexity Product Development Inc., Vancouver, WA (US); Oregon Health & Science University, Portland, OR (US)

(*) Notice: Subject to any disclaimer, the term of this patent is extended or adjusted under 35 U.S.C. 154(b) by 1019 days.

(21) Appl. No.: 14/825,757

(22) Filed: Aug. 13, 2015

(65) Prior Publication Data

US 2016/0045148 A1 Feb. 18, 2016

Related U.S. Application Data

(60) Provisional application No. 62/037,068, filed on Aug. 13, 2014.

(51) Int. Cl.
*A61B 5/15* (2006.01)
*B01L 3/00* (2006.01)
*A61B 5/151* (2006.01)

(52) U.S. Cl.
CPC ...... *A61B 5/150358* (2013.01); *A61B 5/1513* (2013.01); *A61B 5/15019* (2013.01);
(Continued)

(58) Field of Classification Search
CPC ............................................. A61B 5/150358
See application file for complete search history.

(56) References Cited

U.S. PATENT DOCUMENTS 6,261,245 B1 * 7/2001 Kawai ................ A61B 5/15186
600/576
2006/0155215 A1 7/2006 Cha
(Continued)

FOREIGN PATENT DOCUMENTS

JP 2014138891 A 7/2014
KR 20090090659 A 8/2009

OTHER PUBLICATIONS

International Search Report and Written Opinion for International Application No. PCT/US2015/045049; dated Oct. 29, 2015; 14 pages.

*Primary Examiner* — Daniel L Cerioni
*Assistant Examiner* — Yasmeen S Warsi
(74) *Attorney, Agent, or Firm* — Schwabe, Williamson & Wyatt, P.C.

(57) ABSTRACT

Apparatuses and methods for dried blood spot (DBS) sample collection are disclosed. A dried blood spot sampling device is configured to deliver blood through a passage to an absorbent disk in the device and control an amount of blood saturating the absorbent disk. The sampling device may include a manually actuatable component adjustable between a first position, in which an outlet of the passage is not in physical contact with the absorbent disk, and a second position, in which the outlet of the passage is in physical contact with the absorbent disk.

24 Claims, 11 Drawing Sheets

(52) U.S. Cl.
CPC .... *A61B 5/150022* (2013.01); *A61B 5/15113* (2013.01); *A61B 5/15117* (2013.01); *A61B 5/15144* (2013.01); *A61B 5/150213* (2013.01); *A61B 5/150412* (2013.01); *A61B 5/150503* (2013.01); *A61B 5/150832* (2013.01); *A61B 5/150908* (2013.01); *B01L 3/5023* (2013.01); *B01L 3/502715* (2013.01); *B01L 2200/0678* (2013.01); *B01L 2300/069* (2013.01); *B01L 2300/0681* (2013.01); *B01L 2300/0816* (2013.01); *B01L 2300/0838* (2013.01); *B01L 2300/105* (2013.01); *B01L 2400/0406* (2013.01)

(56) References Cited

U.S. PATENT DOCUMENTS

| | | | | |
|---|---|---|---|---|
| 2006/0173380 A1* | 8/2006 | Hoenes | ............... | A61B 5/14532 600/583 |
| 2006/0229530 A1* | 10/2006 | Hosoda | ............ | A61B 5/150022 600/573 |
| 2011/0196218 A1* | 8/2011 | Nomura | ............... | A61B 5/1411 600/365 |
| 2012/0123297 A1 | 5/2012 | Brancazio | | |
| 2012/0277629 A1 | 11/2012 | Bernstein | | |

\* cited by examiner

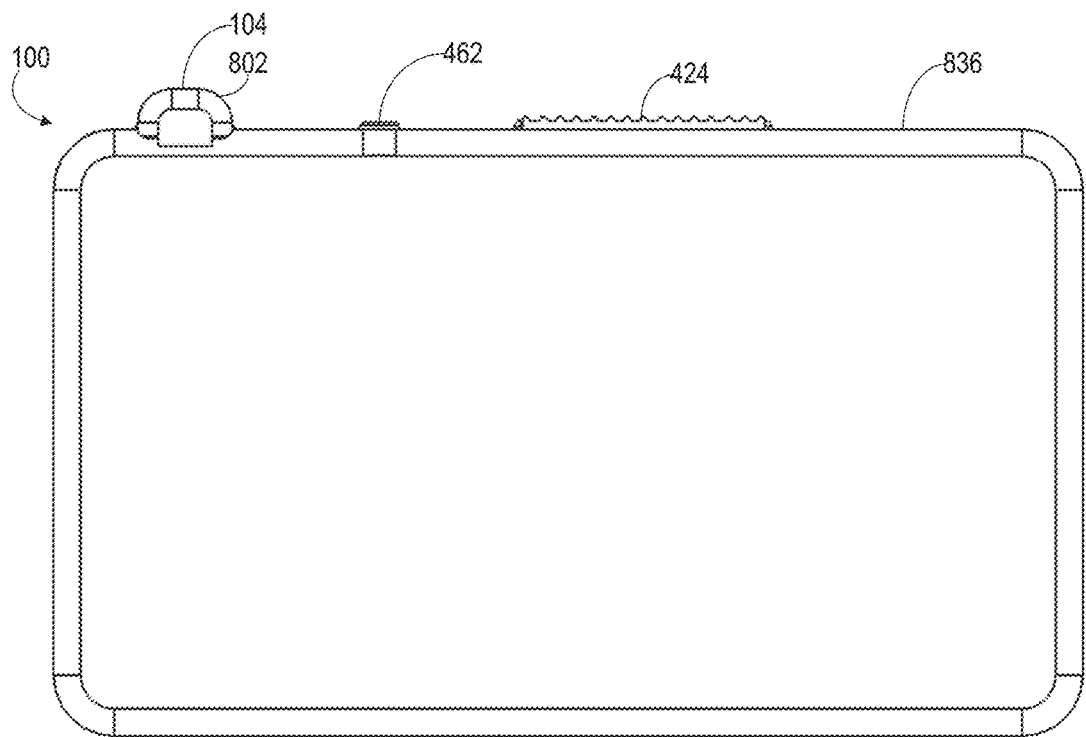
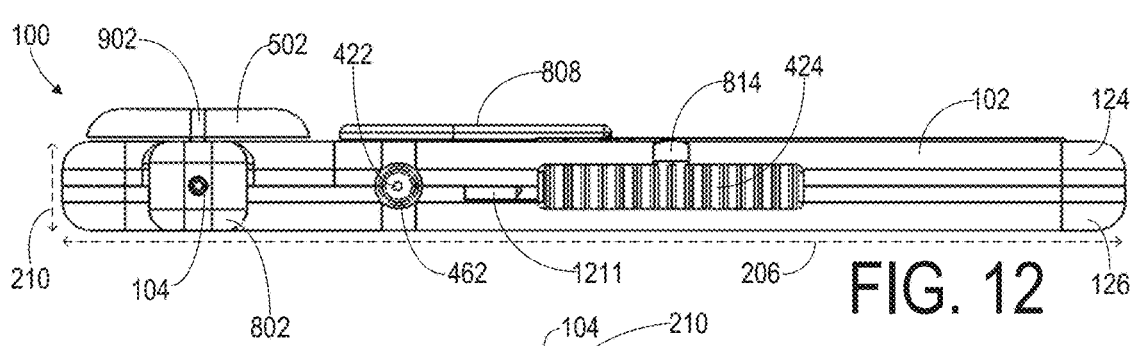
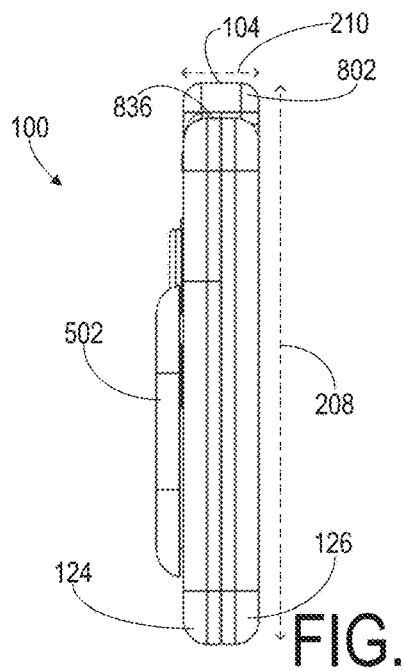

DRIED BLOOD SPOT COLLECTION DEVICE

CROSS REFERENCE TO RELATED APPLICATION

The present application claims priority to U.S. Provisional Patent Application No. 62/037,068, filed Aug. 13, 2014, entitled "DRIED BLOOD SPOT COLLECTION DEVICE," the disclosure of which is hereby incorporated by reference in its entirety.

ACKNOWLEDGMENT OF GOVERNMENT SUPPORT

This invention was made with government support under Grant No. UL1TR000128 awarded by the National Institutes of Health. The government has certain rights in the technology.

FIELD

The present disclosure relates to the field of dried blood spot testing, and, more specifically, to single-use dried blood spot sampling devices.

BACKGROUND

Blood tests may be performed on blood samples for screening, diagnosing, and monitoring various medical conditions. Various approaches are used to collect blood samples for blood tests. Venipuncture is a widely-used blood collection procedure that generally relies on trained medical practitioners, specialized equipment, and sterilization protocols to collect liquid blood samples for processing. Blood samples collected by venipuncture usually are separated by centrifugation and stored under refrigeration.

Another blood sample collection approach is dried blood spot (DBS) sampling. DBS is a form of biosampling in which blood samples are blotted and dried on a suitable absorbent material, e.g., filter paper. In some approaches, a lancet may be used to draw blood, e.g., via a fingerstick, and the blood sample may be transferred to one or more delineated circular regions, or spots, on filter paper. The spotted filter paper with the blood samples may be air dried for several hours to obtain a DBS specimen that may be shipped to an analytical laboratory and analyzed using various methods such as DNA amplification or high-performance liquid chromatography (HPLC). In some approaches, a blood spot on DBS paper may be sampled by punching out a smaller diameter hole in the paper from within the blood spot or tearing off sections of the blood spot. For example, a blood sample may be transferred to a delineated circular region having a diameter of approximately 10 mm on absorbent paper and, during processing, a 3-6 mm hole may be punched out of the 10 mm blood sample spot for analysis. The punched sample may then be placed in a tube and eluted with a buffer so that the extracted sample can undergo various diagnostic tests.

Compared with liquid blood specimens, e.g., as collected via venipuncture, DBS specimens may have a longer lifespan, have a reduced need for refrigeration, pose less of a biohazard risk to handlers, utilize less blood, and be easier to transport or store. Potential applications of DBS sampling include screening, diagnosis, monitoring, and research of various medical conditions/populations including HIV, epilepsy, cancer, transplant patients, etc.

The inventors herein have recognized various issues with current approaches to DBS sampling. In current DBS sampling approaches, biological sample distribution across the collection material is dependent on sample application techniques and can result in uneven analyte concentrations across the material. For example, some approaches require a patient to place a large drop of blood, e.g., about 30 µL, on DBS filter paper in order to attempt to saturate a large area of the filter paper, e.g., a 10 mm spot. Saturating such a large area of the filter paper may lead to a non-homogenous distribution of the blood over the filter paper, which may lead to errors in sample analysis due to inaccurate sample volumes. Additionally, many DBS approaches require a user to physically touch the DBS paper in order to transfer the blood to the paper. However, touching the DBS paper can produce non-uniform blood sample spots, which may also reduce accuracy.

As described above, in some approaches, a sample disk may be punched out from a larger diameter blood spot or sections may be torn off from the blood spot for analysis. However, punching out a sample disk or tearing off sections from a blood spot region of sample paper may lead to increased variability and errors in sample analysis. For example, variable analytical results may occur when a sub-sample within a sample spot is removed manually with a hole-punch or when sections of the blood spot are torn off.

Additionally, many DBS sampling approaches rely on patients and/or clinicians to perform multiple steps that may be cumbersome for use by patients. For example, some approaches require a patient to use a glass capillary tube to draw blood from a lanced finger and then to place the capillary tube containing the blood sample into a holder to saturate a spot on filter paper. Such an approach may be difficult to implement and may additionally lead to uneven blood distribution across the spot and under-saturation or over-saturation of the DBS material. Further, such approaches may require the use of many separate components, such as a lancet, filter papers, a holder for drying, and containers with a drying agent for transport. These separate components can be cumbersome for use even by a skilled technician, and may not suitable for use by a patient alone. Further, such approaches may require disposal of blood collection materials as hazardous waste, e.g., used lancets, capillary tubes, etc.

SUMMARY

The present disclosure is directed to dried blood spot (DBS) collection devices and methods of using such devices. In one example approach, a dried blood spot sampling device is configured to deliver blood through a passage to an absorbent disk in the device, e.g., a 3 mm or 6 mm filter paper disk, and control an amount of blood saturating the absorbent disk. Although examples of circular absorbent disks are often discussed herein, an absorbent disk may have any suitable footprint. The sampling device may additionally include a manually actuatable component adjustable between a first position, where an outlet of the passage is not in physical contact with the absorbent disk, and a second position, where the outlet of the passage is in physical contact with the absorbent disk.

Some embodiments of the DBS collection device may additionally include a lancet system incorporated into the device, thereby providing a self-contained, easy-to-use, and safe method for obtaining a DBS sample. For example, the device can potentially be used remotely and shipped using regular mail to a clinical lab without the need for disposing of or shipping biohazardous components.

For example, in some embodiments, the DBS device may additionally include a single-use, adjustable-depth, retracting lancet incorporated within the device for lancing a finger of a user. After the finger is lanced, the user may place the lanced finger at an inlet of the passage so that blood is drawn into the passage. The user may then actuate the manually-actuatable component to put the outlet of the passage into physical contact with the sample disk so that a precise amount of blood is transferred from the passage to the sample disk to precisely saturate the sample disk. After saturation of the sample disk, the user may release the manually actuatable component so that the outlet is no longer in physical contact with the sample disk. The DBS device may then be sealed and shipped, e.g., via mail, to a testing center, for example.

In such an approach, a precise volume of blood may be delivered via the passage to a specifically-sized sample disk to precisely saturate the disk, thereby providing a reproducible, accurate, and uniform distribution of blood over the disk. In this approach, the sample disk may be sized such that no additional manipulation of the disk, such as tearing off or punching out portions of the disk, are needed to prepare the specimen for testing at a lab. In various embodiments, this may decrease variability and error, and may reduce processing time at the lab. Additionally, such an approach may be less intrusive to the patient and may use a smaller volume of blood compare to previous approaches, such as venipuncture and approaches which attempt to saturate a large dot or substrate, as described above.

Compared to clinical blood collection approaches such as venipuncture, various ones of the approaches disclosed herein have the potential to reduce costs, e.g., phlebotomy costs, and decrease impact on the user. For example, since some embodiments of the devices disclosed herein may be used remotely and then mailed to a clinic, such devices may provide cost savings from travel, fewer points of contact, and decreased barriers to compliance.

This Summary is provided to introduce a selection of concepts in a simplified form that are further described below in the Detailed Description. This Summary is not intended to identify key features or essential features of the disclosed subject matter, nor is it intended to be used to limit the scope of the disclosed subject matter. Furthermore, the disclosed subject matter is not limited to implementations that address any or all disadvantages noted in any part of this disclosure.

BRIEF DESCRIPTION OF THE DRAWINGS

FIG. 11 is a back view of the dried blood spot collection device shown in FIG. 8, in accordance with various embodiments;

FIG. 12 is a side view along a length of the dried blood spot collection device shown in FIG. 8, in accordance with various embodiments;

FIG. 13 is a side view along a width of the dried blood spot collection device shown in FIG. 8, in accordance with various embodiments;

DETAILED DESCRIPTION

The following detailed description is directed to apparatuses and methods for dried blood spot (DBS) sampling. In the following detailed description, reference is made to the accompanying drawings which form a part hereof, and in which are shown, by way of illustration, embodiments that may be practiced. It is to be understood that other embodiments may be utilized and structural or logical changes may be made without departing from the scope of the disclosure. Therefore, the following detailed description is not to be taken in a limiting sense. Various operations may be described as multiple discrete operations in turn, in a manner that may be helpful in understanding embodiments; however, the order of description should not be construed to imply that these operations are order-dependent.

Figure 1:
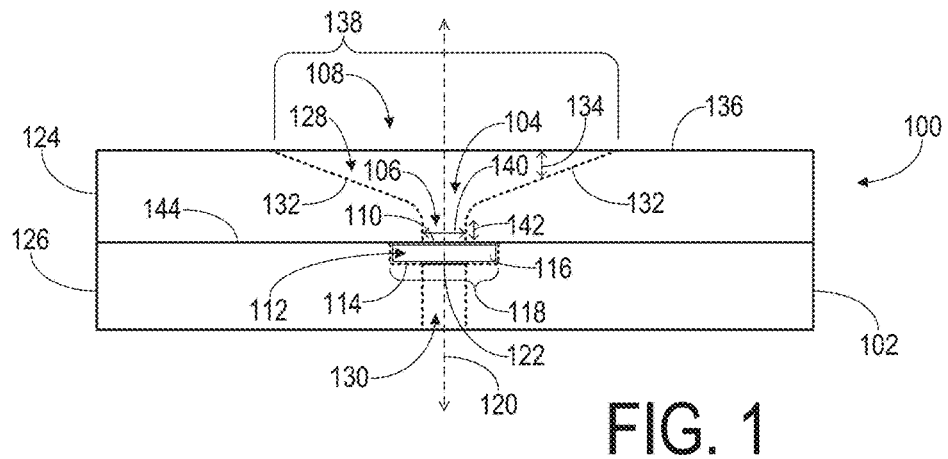
FIG. 1 is a schematic depiction of a side view of an example of a dried blood spot collection device, in accordance with various embodiments.

FIG. 1 is a schematic depiction of a side view of an example embodiment of a DBS collection device 100. DBS collection device 100 includes a body 102 that defines an inlet 104 of a passage 106 extending from an exterior 108 of the body 102 to an outlet 110 in an interior cavity 112 of the body 102. In some embodiments, as shown in the illustrations of FIGS. 1-21, passage 106 may include a capillary passage or capillary tube. However, it should be understood that any suitable passage or orifice may be used without departing from the scope of the present disclosure. For example, as shown in FIG. 22, passage 106 may include a screened orifice. The body 102 may include any suitable material or combination of materials, e.g., plastic, glass, stainless steel, etc.

Figure 3:
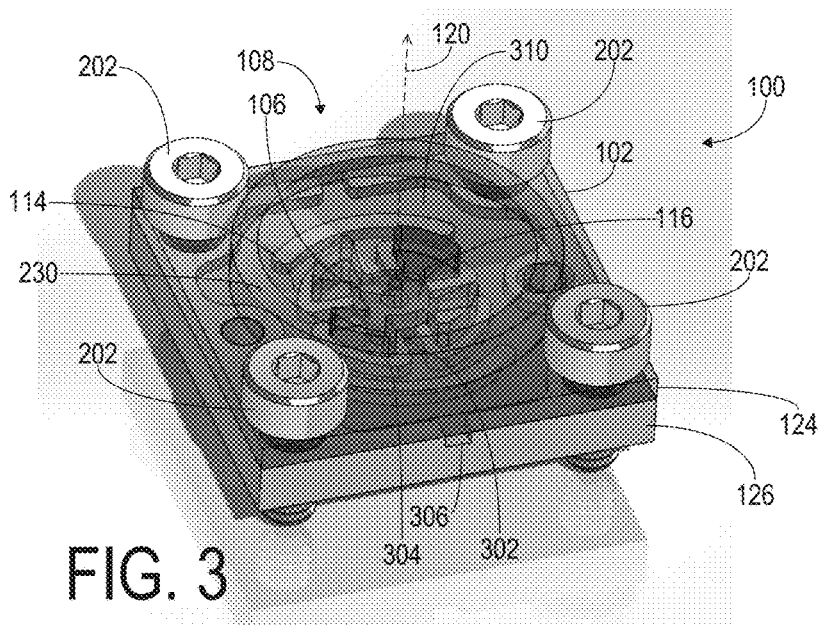
FIG. 3 is another perspective view of an example of a dried blood spot collection device, in accordance with various embodiments.

In the example embodiment shown in FIG. 1, body 102 includes a top plate 124 coupled to a bottom plate 126 which may define the interior cavity 112. Both the top plate 124 and the bottom plate 126 may have similar and/or complementary shapes, e.g., the top and bottom plates may have substantially the same length, width, and thickness. However, in some examples, e.g., as shown in FIG. 3 and described below, the top plate 124 and the bottom plate 126 may have substantially the same length and width but may have different thicknesses. Further, in other examples, the top plate 124 and the bottom plate 126 may have different shapes, e.g., different lengths, widths, and/or thicknesses. The top and bottom plates 124 and 126 may be coupled together in any suitable way. For example, the top and bottom plates 124 and 126 may be affixed to each other via a suitable adhesive and/or via one or more clamps, rivets, bolts, screws, clips, latches, pins, pegs, or other coupling components. In some examples, the top and bottom plates 124 and 126 may be molded together after an installation of various internal components in the top and bottom plates 124 and 126. Example components which may be included within body 102 are described below.

DBS collection device 100 includes a platform 114 coupled to the body 102 within the interior cavity 112. Platform 114 is configured to hold an absorbent disk 116 in a fixed position on a circular region 118 of the platform 114. The absorbent disk 116 may include any suitable DBS material, e.g., a filter paper disk, a porous polymer, etc. In some examples, the absorbent disk 116 may be sized such that no additional manipulation of the absorbent disk, such as tearing off or punching out portions of the absorbent disk 116, are needed to prepare the specimen for testing at a lab. For example, the absorbent disk 116 may include a 3 mm filter paper disk or a 6 mm filter paper disk.

In example illustrated in FIG. 1, platform 114 is formed as a circular cut-out in a top surface 144 of bottom plate 126. The circular cut-out may be sized to receive and hold an absorbent disk (e.g., the absorbent disk 116) of a predetermined size, e.g., a 3 mm or 6 mm diameter. Platform 114 is positioned directly beneath capillary outlet 110 of passage 106 so that a central axis 120 of the passage 106 is normal to, i.e., is perpendicular to or forms a right angle with, the platform 114 and intersects the center 122 of the circular region 118 of the platform 114.

In the example embodiment shown in FIG. 1, a funnel-shaped indentation 128 is included in the top surface 136 of the top plate 124 of body 102. Indentation 128 is defined by inwardly sloping walls 132 which form a funnel shape to assist in positioning a fingertip above the capillary inlet and to direct blood samples from a lanced finger placed into the indentation 128 into the capillary inlet 104. The depth 134 of walls 132 of indentation 128 from top surface 136 decreases with increasing distance from the capillary inlet 104, thereby forming a funnel in the top plate 124 for directing a blood sample introduced at the indentation 128 into the capillary inlet 104. At the indentation 128, the top surface 136 is recessed and slopes inwardly toward the capillary inlet 104. As shown in FIGS. 2, 16, 17, and 22, and described below, in some examples, the indentation 128 may be substantially circular in shape when viewed from above so as to function as a funnel for finger positioning and directing a blood sample into the passage 106. The indentation 128 may be sized to encompass and position a fingertip in a predetermined location. For example, a diameter 138 of the indentation at the top surface may be at least 1.5 cm. The diameter of the indentation 128 may decrease from the diameter 138 at the top surface 136 to a diameter 140 of capillary inlet 104.

The passage 106 may have a predetermined length 142 along the central axis 120. The length 142 and diameter 140 of the passage 106 may be specifically sized to hold a predetermined amount of blood for delivery to the absorbent disk 116. For example, the length 142 and diameter 140 of the passage 106 may be sized to hold a volume of blood substantially equal to a volume of blood that would sufficiently saturate the absorbent disk 116. The amount of saturation that is "sufficient" may depend on the test being run (e.g., with a mass spectrometer configured to analyze the blood). In some embodiments, 7.4 microliters may be a sufficient amount. In some examples, the passage 106 may be sized to hold a volume of blood greater by a predetermined amount (e.g., a fixed volume or percentage) than the volume of blood which would sufficiently saturate the absorbent disk 116. In some embodiments, the dimensions of the absorbent disk 116 may be selected to allow the absorbent disk 116 to hold a predetermined volume of blood, and thereby utilize the absorbent disk 116 as a metering device for the amount of blood stored therein. In various embodiments, the nominal value of this predetermined volume may depend on the particular test to be performed on the blood, as noted above with reference to the passage 106.

In the example embodiment shown in FIG. 1, the lower plate 126 defines an air vent channel 130 positioned directly below the absorbed disk 116. The air vent channel 130 may include an aperture extending through the bottom plate in a direction along the central axis 120. The air vent channel 130 may share a central axis with passage 106, e.g., central axis 120 may be a central axis of both the passage 106 and the air vent channel 130. When included, the air vent channel 130 may provide ventilation to the interior cavity 112 to assist in drying a blood sample delivered to the absorbent disk 116, and may provide a pathway for excess blood not absorbed by the absorbent disk 116.

Figure 2:
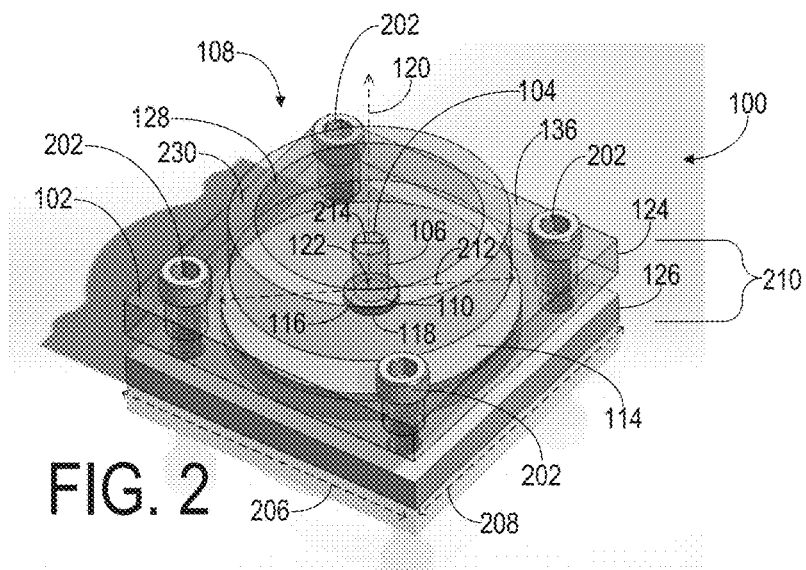
FIG. 2 is a perspective view of another example of a dried blood spot collection device, in accordance with various embodiments.

FIG. 2 is a perspective view of another example embodiment of a DBS collection device 100. Like-numbered elements shown in FIG. 2 correspond to like-numbered elements shown in FIG. 1 and described above. DBS device 100 shown in FIG. 2 includes a body 102 having a length 206, a width 208, and a thickness 210. As shown in FIG. 2, the length 206 may be substantially the same as the width 208 and both the length 206 and the width 208 may be greater than the thickness 210, e.g., the thickness 210 may be at least 4 times smaller than both the length 206 and width 208. However, in other examples, the length 206 may be greater than the width 208 or the width 208 may be greater than the length 206.

In the example embodiment shown in FIG. 2, the platform 114 includes an absorbent or porous material mounted on the top surface 144 of the bottom plate 126. Other example embodiments wherein the platform 114 includes an absorbent or porous material are shown in FIGS. 16-22 and described below. The absorbent or porous material may be a porous polymer material, absorbent paper, or any other suitable absorbent or porous material which functions to absorb excess blood that is not absorbed into the absorbent disk 116. As described in more detail below, in various embodiments, the platform 114 may have physical properties that serve to balance capillary forces between the absorbent disk 116 and the platform 114 so that excess blood in the absorbent disk 116 is wicked into the platform 114 so that the absorbent disk 116 is saturated with a precise amount of blood for testing. As noted above, the platform 114 may include an absorbent material positioned below the absorbent disk 116 and in physical contact with a bottom portion of the absorbent disk 116. In various embodiments, the absorbent material of the platform 114 may be a different material than the absorbent disk 116, or may be a same material as absorbent disk 116, but the absorbent disk 116 and the absorbent material of the platform 114 are two different components.

Characteristics of the absorbent material included in the platform 114, e.g., average pore size, porosity, shape, volume, surface area, etc., may be selected to provide a balance of relative capillary forces between the absorbent disk 116 and the platform 114 such that blood in excess of a predetermined absorbent disk saturation volume is drawn from the absorbent disk 116 into the platform 114. As one non-limiting example, the platform 114 may include an absorbent disk composed of an absorbent material with a diameter 212 greater than the diameter 214 of the absorbent sample disk 116. In some examples, diameter 212 may be at least twice as large as diameter 214. However, in other examples, diameter 212 may be less than or substantially equal to diameter 214. In this example, the platform 114 comprising the absorbent material may be positioned and sandwiched between the top plate 124 and bottom plate 126. As noted above, the top and bottom plates 124 and 126 may be coupled together in any suitable way. In the example illustrated in FIG. 2, the top plate 124 and bottom plate 126 are shown coupled together by a plurality of coupling elements 202 positioned adjacent to an outer perimeter of body 102. As one example, the coupling elements 202 may include screws, e.g. machine screws, threaded directly into the bottom plate 126. As another example, the coupling elements 202 may include nuts coupled to bolts which extend through apertures in the top and bottom plates 124 and 126. It should be understood that any suitable coupling components may be used to hold the top and bottom plates 124 and 126 together, e.g., bolts, screws, clamps, rivets, clips, latches, pins, pegs, etc. In some examples, other approaches may be used to couple the top and bottom plates 124 and 126 together without external fasteners. For example, the top and bottom plates 124 and 126 of the DBS collection device 100 may be snapped together with plastic features extending from of each half and/or an adhesive or ultrasonic welding may be used to couple the top and bottom plates 124 and 126 together. When the top and bottom plates 124 and 126 are coupled together, they hold the platform 114 and the absorbent disk 116 in a fixed position below the passage 106.

The embodiment shown in FIG. 2 also includes an indentation 128 which assists in positioning a lanced finger and directing blood from the lanced finger into the passage 106 and onto the absorbent disk 116. However, in this example, indentation 128 is formed in a raised portion 230 of the top plate 124 and extends a non-zero distance above the top surface 136 of the top plate 124. In this example, the raised portion 230 takes the form of a cylinder coupled to top surface 136 at a base of the cylinder. The interior of the cylinder includes walls which taper inwardly to form a funnel which assists in finger positioning and directing a blood sample into the passage 106. Excess blood not absorbed by the absorbent disk 116 may be absorbed by the platform 114 comprising the porous or absorbent material. Since the platform 114 is configured to absorb excess blood in this example, occurrences of oversaturation of the absorbent disk 116 may be reduced, thereby potentially increasing accuracy when the DBS sample is processed for testing.

FIG. 3 is a perspective view of another example embodiment of a DBS collection device 100. Like-numbered elements shown in FIG. 3 correspond to like-numbered elements shown in FIGS. 1 and 2 and described above. In the example embodiment shown in FIG. 3, the platform 114 includes a plurality of capillary channels 302 formed from raised regions 304 in the top surface 144 of the bottom plate 126. The capillary channels 302 radiate outwardly in the top surface 144 of the bottom plate 126 from beneath the absorbent disk 116 and open into larger channels 310 formed in the bottom plate 126. The capillary channels 302 may wick excess blood away from the absorbent disk 116 in order to reduce uneven saturation of the absorbent disk. For example, the capillary channels 302 may be sized to provide a balance of relative capillary forces between the absorbent disk 116 and the capillary channels 302 such that blood in excess of a predetermined absorbent disk saturation volume (e.g., a fixed volume or percentage) is drawn from the absorbent disk 116 into the capillary channels 302. Additionally, the capillary channels 302 may assist in accelerating drying of a blood sample transferred to the absorbent disk 116. In some examples, one or more air vents 306 may be included in the body 102. The air vents 306 may be formed as grooves or slots in the top surface 144 of the bottom plate 126 and may be in communication with the capillary channels 302 to assist in drying blood in the absorbent disk 116 and in the capillary channels 302. Any suitable design and any number of capillary channels 302 may be used without departing from the scope of the present disclosure. The example shown in FIG. 3 shows four capillary channels 302 which extend from central axis 120 toward an outer perimeter of the body 102 and open into larger channels 310 positioned outside of a footprint of the absorbent disk 116. Raised regions 304 in the bottom plate may extend below the absorbent disk 116 to support the absorbent disk 116 in a fixed position directly beneath the passage 106.

Figure 4:
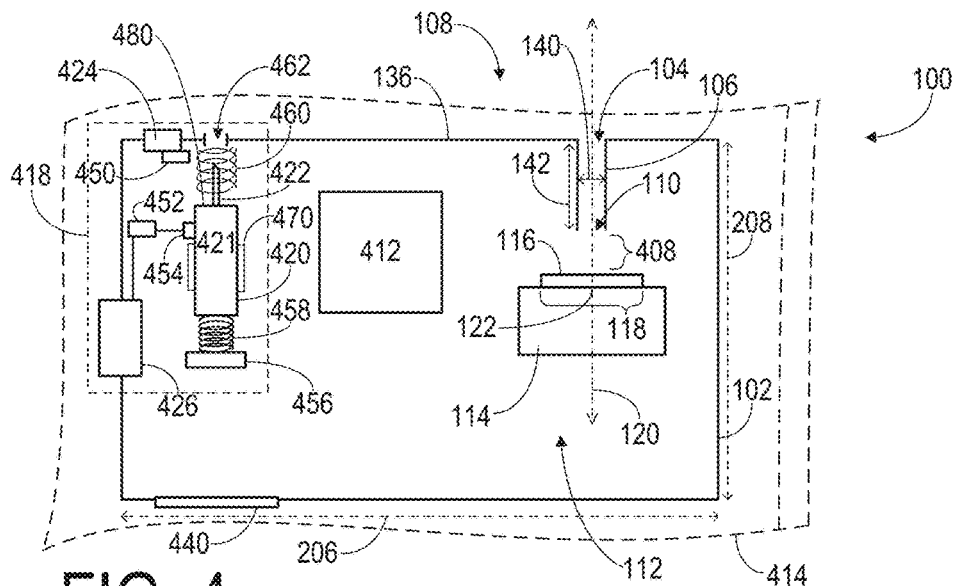
FIG. 4 is a schematic depiction of an example of a dried blood spot collection device, in accordance with various embodiments.

FIG. 4 shows a schematic depiction of another example embodiment of a DBS collection device 100. In this example, DBS collection device 100 additionally includes a lancet system 418 described in more detail below. It should be understood that inclusion of a lancet system in DBS collection device 100 is optional and, in some embodiments, a lancet system may be omitted. Like-numbered elements shown in FIG. 4 correspond to like-numbered elements shown in FIGS. 1-3 and described above.

The DBS collection device 100 shown in FIG. 4 includes a body 102 that defines an inlet 104 of a passage 106 extending from an exterior 108 of the body 102 to an outlet 110 in an interior cavity 112 of the body 102. As remarked above, passage 106 may include any suitable passage or orifice, e.g., a capillary passage or a screened orifice. The body 102 may include any suitable material and may have a variety of dimensions and shapes, additional examples of which are described below.

The DBS collection device 100 shown in FIG. 4 includes a platform 114 coupled to the body 102 within the interior cavity 112 of the body 102. Platform 114 is configured to hold a specifically-sized absorbent disk 116 in a fixed position on a circular region 118 of the platform 114. In the illustrated embodiment, platform 114 is positioned directly beneath outlet 110 of passage 106 so that a central axis 120 of the passage 106 is normal to the platform 114 and intersects the center 122 of the circular region 118 of the platform 114. The passage 106 may have a predetermined length 142 along the central axis 120 and a predetermined diameter 140 or gauge. For example, the length 142 and diameter 140 of the passage 106 may be specifically sized to hold a predetermined amount of blood for delivery to the absorbent disk 116.

In some examples, the DBS collection device 100 may include a desiccant 412 in interior cavity 112 to assist in drying blood transferred to the absorbent disk 116 and to maintain a reduced humidity level inside the DBS collection device 100. Desiccant 412 may include any suitable hygroscopic substance that induces or sustains a state of dryness. Example desiccants include silica, activated charcoal, calcium sulfate, calcium chloride, molecular sieves, etc. Desiccant 412 may be mounted to or coupled within the interior cavity 112 of body 102 at any suitable location and in any suitable way. In some examples, an inner wall of body 102 may include one or more desiccant mounting components for holding desiccant 412 in a fixed position in the interior cavity 112.

The DBS collection device 100 may optionally include a lancet system 418. Lancet system 418 may include a lancet 420 having a needle 422 extending from a body 421 of the lancet 420, a lancet actuation component 426, a lancet depth adjustment component 424, and a lancet port 462 formed as an opening in an outer wall of body 102. The needle 422 may have any suitable length and gauge. For example, the needle 422 may have a gauge of approximately 23. In some examples, the length of the needle 422 used may be selected based on a desired or nominal needle penetration depth. As an example, the selected needle length may be such that the needle 422 extends a distance of approximately 2 mm out of body 102 when actuated.

The lancet 420 may be slidably mounted in the interior cavity 112 of body 102 and in communication with the lancet actuation component 426 such that when the lancet actuation component 426 is manually actuated, a portion of the needle 422 is projected out through the lancet port 462 and into the exterior 108 of the body 102. For example, the lancet system 418 may include a biasing spring 458 which is coupled to or interfaces with a base component 456 affixed within the interior cavity 112 of body 102. The biasing spring 458 may be in contact with a base portion of lancet 420, e.g., a side of lancet 420 opposing needle 422, to bias the lancet 420 toward the lancet port 462. In particular, the biasing spring 458 may supply a biasing force to the lancet 420 in a direction along a central axis of the needle 422 of the lancet 420 towards the lancet port 462.

In some examples, the spring-biased lancet 420 may be held in a trigger-ready position within the interior cavity 112 by a latch 454 coupled to the lancet actuation component 426. For example, in the trigger-ready position, the biasing spring 458 may be compressed between the lancet 420 and the base component 456 to confer a potential energy to the biasing spring 458 which may be released, e.g., transformed to kinetic energy, in response to removal of the latch 454. Actuation of the lancet actuation component 426 may release the latch 454 from the lancet 420, thereby permitting the biasing spring 458 to propel the lancet 420 so that the needle 422 of the lancet 420 protrudes out of the lancet port 462 by a predetermined distance. For example, the lancet actuation component 426 may include a button which extends at least partially into the exterior 108 of body 102 so that a user can engage or press the button in order to actuate the lancet 420.

The lancet 420 may be slidably mounted within tracks 470 mounted within the interior cavity 112 such that the lancet 420 is moveable within the interior cavity 112 between a first position where the needle 422 is fully contained within the interior cavity 112 or does not protrude out of the lancet port 462 and a second position where a length of the needle 422 extends outside of the lancet port 462. As an example, the lancet 420 may include slots or grooves which are complementary to tracks 470 so that the lancet 420 can slide within the tracks 470 between the first and second positions. In some examples, the length of the portion of the needle 422 projected out of the lancet port 462 may be adjusted via a manual adjustment of the lancet depth adjustment component 424. For example, the lancet depth adjustment component 424 may include one or more blocking elements 450 that interface with a portion of the lancet 420 to control the length of the needle 422 that protrudes out of the lancet port 462 following actuation of the lancet 420. In some embodiments, the lancet depth adjustment component 424 may include a slidable component extending at least partially outside of body 102. Adjustment of the lancet depth adjustment component 424 may include sliding a blocking element 450 into a path extending parallel to the central axis of needle 422 from a position on a top surface 480 of the body 421 adjacent to a base of needle 422. When slid into such a position, the blocking element 450 may decrease the length of the needle 422 which protrudes from the lancet port 462, thereby decreasing a penetration depth of the needle 422 into a finger positioned on the lancet port 462 when the lancet 420 is actuated.

In some examples, lancet system 418 may be a single-use lancet system, such that, after an initial actuation of the lancet 420 which causes the needle 422 to protrude out of the lancet port 462, the needle 422 automatically retracts back into the interior cavity 112 and stays in the interior cavity 112 during subsequent lancet actuation attempts following the initial actuation. For example, the lancet actuation component 426 may include a breakable component 452 which breaks or becomes non-functional, i.e., no longer operable to actuate the lancet 420, after an initial actuation of the lancet 420 so that the lancet actuation component 426 is no longer functional following the initial actuation.

In some examples, the lancet system 418 may include a counter-biasing spring 460 which interfaces with the lancet 420 to retract the needle 422 after actuation of the lancet 420. For example, a first end of the counter-biasing spring 460 may be in contact with top surface 480 of lancet body 421 and a second end of the counter-biasing spring 460, opposing the first end, may be in contact with an inner surface of body 102 at a position adjacent to lancet port 462. The counter-biasing spring 460 may bias the lancet 420 away from the lancet port 462. In particular, the counter-biasing spring 460 may supply a counter-biasing force to the lancet 420 in a direction along a central axis of the needle 422 of the lancet 420 away from the lancet port 462. In some embodiments, the counter-biasing force provided by the counter-biasing spring 460 may be less than the biasing force provided by the biasing spring 458. For example, a spring constant of the counter-biasing spring 460 may be less than a spring constant of the biasing spring 458. The spring constant of the counter-biasing spring 460 relative to the spring constant of the biasing spring 458 may be such that, following an initial protrusion of the needle 422 out of the lancet port 462, the lancet 420 returns to an equilibrium position governed by the spring constant of the biasing spring 458 and the spring constant of the counter-biasing spring 460. In the equilibrium position, the needle 422 of the lancet 420 may be fully contained inside the interior cavity 112 of the body 102 and/or may not extend outside of the lancet port 162.

In some examples, DBS collection device 100 may include packaging 414. Packaging 414 may include any suitable packaging components which seal the body of the DBS collection device 100, e.g., packaging 414 may include a plastic bag or container. For example, the packaging 414 may be used to form a watertight seal around the DBS collection device 100, provide UV protection of the DBS collection device 100, and/or provide insulation to the DBS collection device 100, etc. As an example, following manufacture of DBS collection device 100, the DBS collection device 100 may be sealed in a suitable watertight protective bag or container providing the packaging 114. In order to use the DBS collection device 100, a user may unseal the DBS collection device 100 by opening the packaging 114 and removing the body 102 from the packaging 114. After a blood sample is delivered to the absorbent disk 116 in the device 100, the user may then reseal the DBS collection device 100 using a suitable bag or container so that the sealed DBS collection device 100 can be transported to a testing facility.

In some examples, DBS collection device 100 may include indicia 440 on one or more regions of an exterior surface of the body 102. For example, the indicia 440 may include one or more of markings, symbols, serial numbers bar codes, optical labels, etc. The indicia may be used to label or identify information associated with the DBS collection device 100 and/or information associated with a user of the DBS collection device 100. As another example, indicia 440 may be included adjacent to lancet depth adjustment component 424 to indicate different lancet needle depth options as shown in FIGS. 8, 10, 16-18, and 22 and described below.

In some embodiments, the DBS collection device 100 may include a manually actuatable component mounted in the body 102 configured to adjust the position of the absorbent disk 116 relative to the outlet 110. In particular, the manually actuatable component may be adjustable between a first position and a second position relative to the body 102. In the first position, when an absorbent disk 116 is mounted in a fixed position on the circular region 118 of the platform 114, the outlet 110 is not in physical contact with the absorbent disk 116 so that there is a non-zero distance 408 between the outlet 110 and a top surface of the absorbent disk 116. In the second position, when an absorbent disk 116 is mounted in the fixed position on the platform 114, the outlet 110 is in physical contact with the absorbent disk 116, i.e., edges of the passage 106 at the outlet 110 opening touch the surface of the absorbent disk 116.

The manually actuatable component may be included in DBS collection device 100 in a variety of ways, some examples of which are described below. In one example shown in FIG. 5, a manually actuatable component 502 may include or be coupled to platform 114 such that actuation of the manually actuatable component 502 causes the platform 114 to move toward the outlet 110 in a direction along the central axis 120 of the passage 106 until the absorbent disk 116 on the platform 114 is in physical contact with, e.g. physically touches, the outlet 110. In this example, manually actuatable component 502 is adjustable between a first position and a second position relative to the body 102, wherein, in the first position when an absorbent disk 116 is mounted in a fixed position on the circular region 118 on the platform 114, the outlet 110 is not in physical contact with the absorbent disk 116 (e.g., does not touch the absorbent disk 116 as shown in FIG. 4), and, in the second position when an absorbent disk 116 is mounted in the fixed position on the platform 114, the outlet 110 is in physical contact with the absorbent disk 116 (e.g., edges defining the opening of the outlet 110 touch a top surface of the absorbent disk 116 as shown in FIG. 5).

Figure 5:
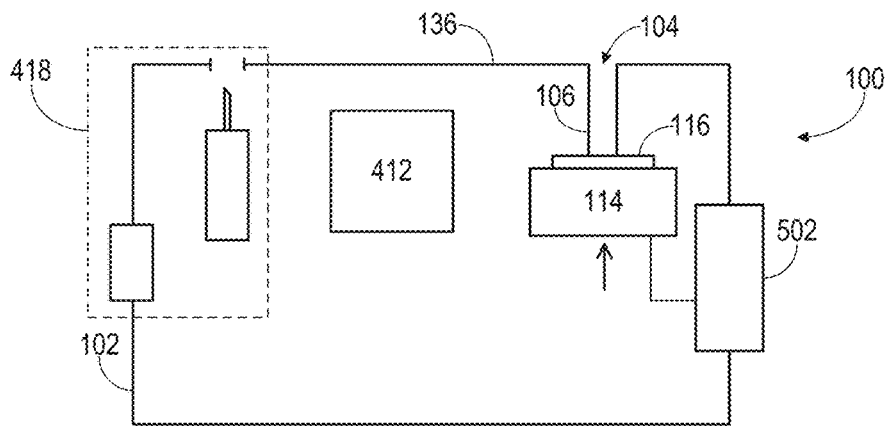
FIG. 5 is another schematic depiction of an example of a dried blood spot collection device, in accordance with various embodiments.

In the example schematically shown in FIG. 5, manually actuatable component 502 may be coupled to platform 114 in any suitable way. For example, manually-actuatable component 502 may be physically connected to platform 114 or otherwise in communication with platform 114 so that a force applied to manually actuatable component 502 is transferred or communicated to platform 114 to move the platform toward outlet 110. Manually actuatable component 502 may at least partially extend outside the body of the DBS collection device 100 and may take the form of a button, lever, slider, etc. In some examples, manually-actuatable component 502 may be biased, e.g., via a spring, to remain in the first position in the absence of actuation or force applied to manually actuatable component 502. Examples of the manually actuatable component 502 schematically shown in FIG. 5 are described below with reference to FIGS. 7-15.

Figure 6:
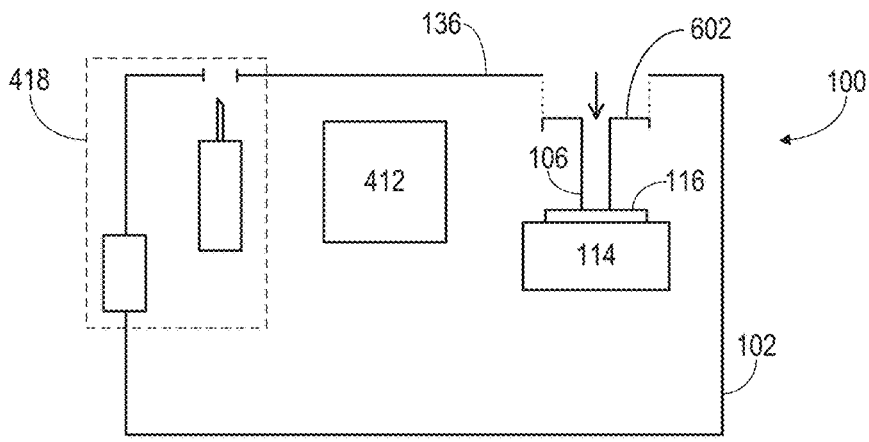
FIG. 6 is another schematic depiction of an example of a dried blood spot collection device, in accordance with various embodiments.

As another example, as shown in FIG. 6, a manually actuatable component 602 may include a region of the body 102 adjacent to and including the passage 106 such that actuation of the manually actuatable component 602 causes the passage 106 to move toward the platform 114 until the outlet 110 is in physical contact with the absorbent disk 116 on the platform 114. In this example, manually actuatable component 602 is adjustable between a first position and a second position relative to the body 102, wherein, in the first position when an absorbent disk 116 is mounted in a fixed position on the circular region 118 on the platform 114, the outlet 110 is not in physical contact with the absorbent disk (as shown in FIG. 4), and, in the second position when an absorbent disk 116 is mounted in the fixed position on the platform 114, the outlet 110 is in physical contact with the absorbent disk 116 (as shown in FIG. 6).

In the example shown in FIG. 6, the platform 114 remains in a fixed position while the passage 106 is moveable relative to body 102 via actuation of manually actuatable component 602. For example, when a lanced finger is placed onto manually actuatable component 602 above passage 106 and used to apply a force to the manually actuatable component 602 in a direction toward platform 114 along the central axis 120 of the passage 106, the passage 106 is moved downward toward platform 114 until the outlet 110 is in physical contact with absorbent disk 116 mounted on platform 114. In some examples, manually actuatable component 602 may be biased, e.g., via a spring, to remain in the first position in the absence of actuation or force applied to manually actuatable component 602. Examples of the manually actuatable component 602 schematically shown in FIG. 6 are described below with reference to FIGS. 16-22.

The manually actuatable component, e.g., component 502 or 602 described above, may be used to selectively deliver a metered amount of blood contained in the passage 106 to the absorbent disk 116 for a duration. As remarked above, in some examples, in absence of actuation or force applied to the manually actuatable component, the outlet 110 of the passage 106 may not be in physical contact with the absorbent disk 116, e.g., the outlet 110 may be separated from the absorbent disk 116 by a non-zero distance. By keeping the outlet 110 separated from the absorbent disk 116 after transfer of the blood sample, occurrences of uneven saturation or oversaturation of the absorbent disk 116 may be reduced. In some examples, the DBS collection device 100 may include a window (examples of which are shown in FIGS. 7-10, 19, and 21 and described below) that allows a user to visually inspect a transfer of blood from the passage 106 to the absorbent disk 116. For example, the user may actuate the manually actuatable component so that the outlet 110 is placed in physical contact with the absorbent disk 116 to facilitate transfer of a blood sample in the passage 106 to the absorbent disk 116. Upon visual identification of saturation of the absorbent disk 116 via the window, the user may discontinue actuation of the manually actuatable component so that the outlet 110 is no longer in physical contact with the absorbent disk 116. Identification of saturation of the absorbent disk 116 while the manually actuatable component is activated may be achieved in a variety of ways. For example, instructions may be provided to a user to maintain actuation of the manually actuatable component to transfer blood from the passage 106 to the absorbent disk 116 for a predetermined period of time. As another example, DBS collection device 100 may include one or more sensors and/or timers used to detect and or identify sufficient saturation of the absorbent disk 116. In this example, the DBS collection device 100 may be configured to output a notification, e.g., a visual or audio notification, to the user to discontinue actuation of the manually actuatable component in response to a detection or identification of sufficient saturation of the absorbent disk 116.

Figure 7:
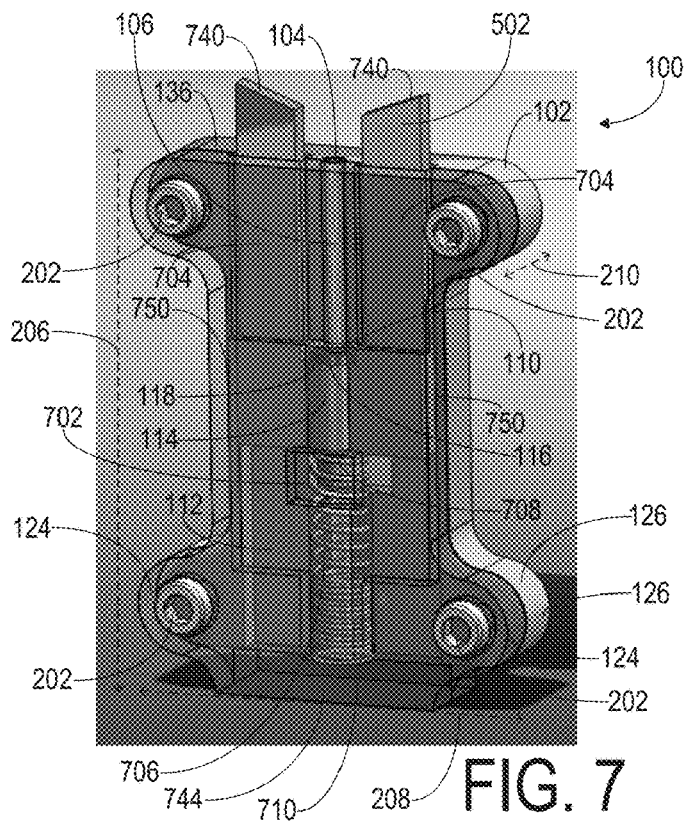
FIG. 7 is a perspective view of an example of a dried blood spot collection device, in accordance with various embodiments.

FIG. 7 is a perspective view of another example embodiment of a DBS collection device 100. Like-numbered elements shown in FIG. 7 correspond to like-numbered elements shown in FIGS. 1-6 and described above. The DBS collection device 100 shown in FIG. 7 includes a body 102, having a length 206, width 208, and thickness 210, that forms an "I" shaped device. Coupling elements 202 couple together the top plate 124 and the bottom plate 126 at regions of the body 112 which extend outwardly at the corners of the DBS collection device 100.

The DBS collection device 100 shown in FIG. 7 includes a manually actuatable component 502 that includes wings 704 coupled to opposing sides of platform 114 and extending upward in a direction along a central axis of passage 106 to partially protrude out of the top surface 136 of the body 102 at opposing positions adjacent to inlet 104. The ends of the protruding portions 740 of the wings 704 of the manually actuatable component 502 are slanted inwardly toward the inlet 104. The manually actuatable component 502 shown in FIG. 7 is spring-biased via a spring 706 positioned between the base 708 of the platform 114 and an internal surface 710 in the interior cavity 112 at a bottom portion 744 of the DBS collection device 100. The spring 706 exerts an upward force on the platform 114 and wings 704 so that, in a resting position, the outlet 110 of the passage 106 is in physical contact with an absorbent disk 116 mounted in a fixed position on a circular region 118 of the platform 114.

The manually actuatable component 502 is slidably mounted in the interior cavity 112 of the body 102 via opposing inner walls 750 which interface with outer edges of the wings 704 of the manually actuatable component 502. In this example, actuation of the manually actuatable component 502 causes the platform 114 to move away from the outlet 110 in a direction along the central axis of the passage 106 so that physical contact between the outlet 110 and the absorbent disk 116 is discontinued, e.g. such that there is a non-zero distance between the outlet 110 and the absorbent disk 116 when the manually actuatable component 502 is engaged. For example, a user may place a lanced finger above the inlet 104 to engage the protruding portions 740 of wings 704. The user may then exert a downward force onto the protruding portions 740 of wings 704 so that the manually actuatable component 502 is pushed in a downward direction such that the outlet 110 is not in physical contact with the absorbent disk 116. The user may continue applying the downward force to protruding portions 700 of wings 704 until the lanced finger interfaces with the inlet 104 to transfer blood from the lanced finger into the passage 106 while the absorbent disk 116 is not in contact with the outlet 110. The user may continue transferring blood from the lanced finger to the passage 106 in this way until the passage 116 is sufficiently filled with a blood sample. As remarked above, in some examples, a diameter and length of the passage 106 may be sized to contain a predetermined amount of blood such that, once the passage 106 is filled with the predetermined amount of blood, no further transfer of blood from the lanced finger into the passage 106 may occur. After transferring blood to the passage 106, the user may disengage the manually actuatable component 502 by discontinuing application of the downward force applied to the protruding portions 740 of wings 704. In some embodiments, after the user disengages the manually actuatable component 502, the manually-actuatable component 502 returns to its spring-biased resting position in which the outlet 110 is in physical contact with the absorbent disk 116 so that blood contained in the passage 106 is transferred to the absorbent disk 116 to saturate the absorbent disk 116.

The DBS device 100 shown in FIG. 7 additionally includes a window 702 which allows a user to visually inspect the absorbent disk 116 during certain conditions. In this example, the window 702 is formed in a wall of body 102 at a position below the absorbent disk 116 when the manually actuatable component 502 is in the resting position, e.g., not actuated. After actuation of the manually-actuatable component 502 to transfer blood into the passage 106, the user may disengage the manually actuatable component 502 so that transfer from the passage 106 to the absorbent disk 116 occurs while the absorbent disk 116 is out of view of the window 702. In order to see if the absorbent disk 116 is sufficiently saturated, the user may then re-engage/actuate the manually actuatable component 502 so that the absorbent disk 116 comes into view via window 702. If, via visual inspection of the absorbent disk 116 via the window 702, the user determines that the absorbent disk 116 is not sufficiently saturated with blood, the user may add an additional amount of blood to the passage 106 for transfer to the absorbent disk 116 as described above.

Figure 8:
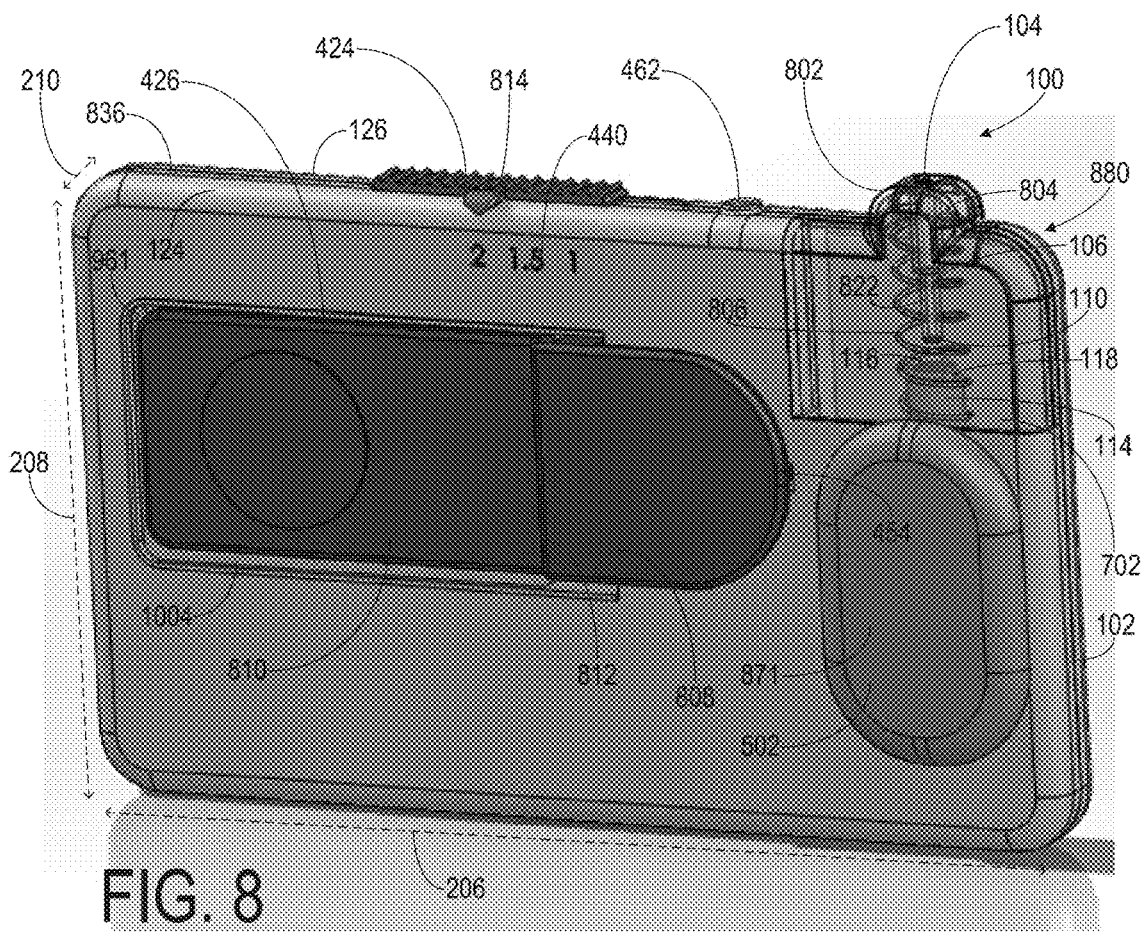
FIG. 8 illustrates a front perspective view of another example of a dried blood spot collection device, in accordance with various embodiments.
Figure 9:
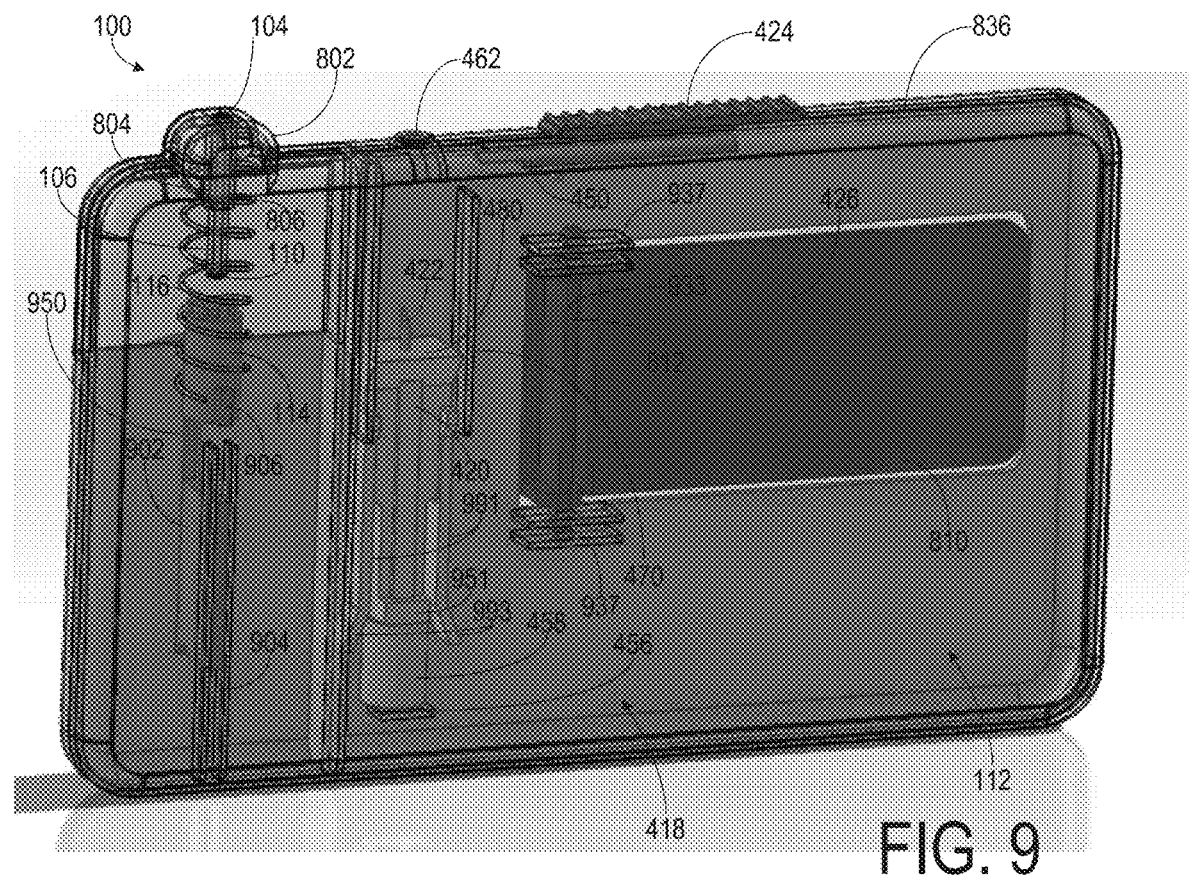
FIG. 9 is a back perspective view of the dried blood spot collection device shown in FIG. 8, in accordance with various embodiments.
Figure 10:
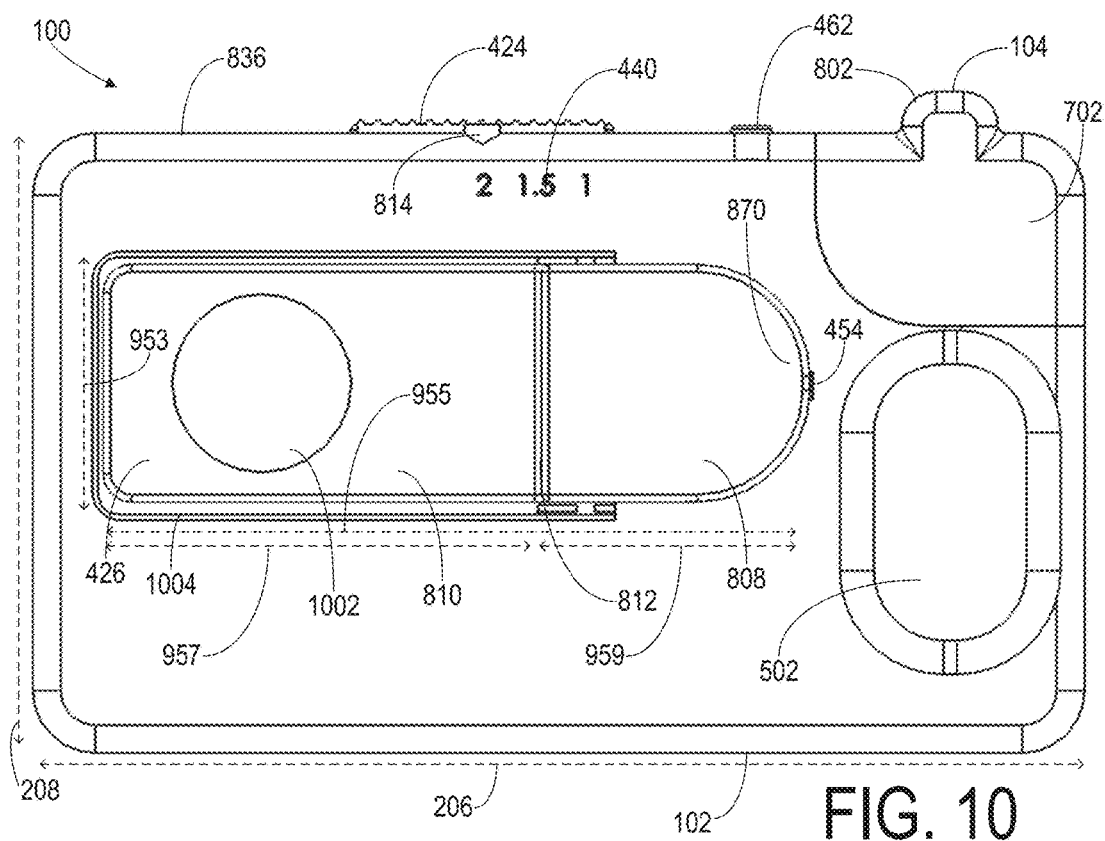
FIG. 10 is a front view of the dried blood spot collection device shown in FIG. 8, in accordance with various embodiments.
Figure 14:
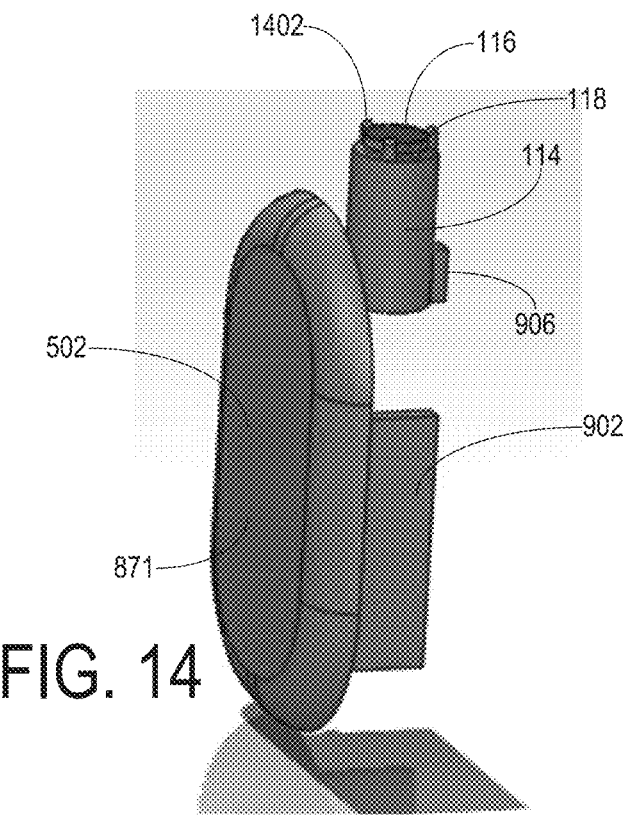
FIG. 14 is a detail view of the manually actuatable component included in the example device shown in FIG. 8, in accordance with various embodiments.
Figure 15:
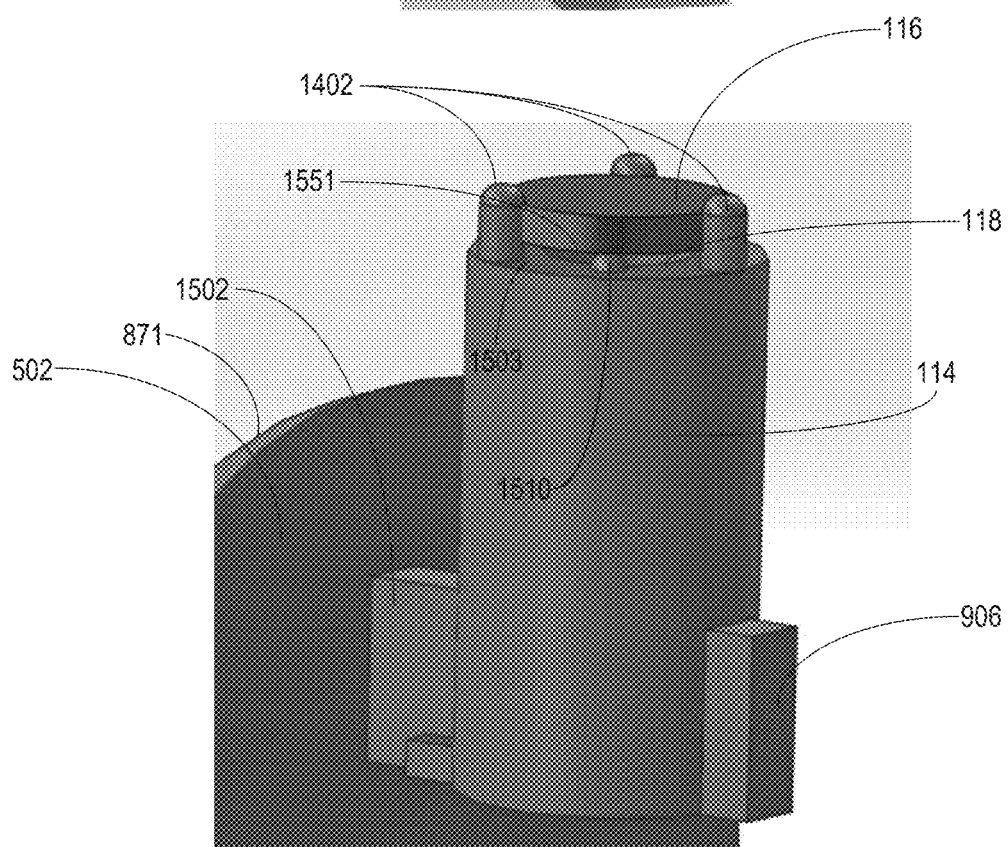
FIG. 15 is another detail view of the manually actuatable component included in the example device shown in FIG. 8, in accordance with various embodiments.

FIGS. 8-13 are various views of another example embodiment of a DBS collection device 100 having a manually actuatable component 502. In particular, FIG. 8 is a front perspective view of DBS collection device 100, FIG. 9 is a back perspective view of DBS collection device 100, FIG. 10 is a front view of DBS collection device 100, FIG. 11 is a back view of DBS collection device 100, FIG. 12 is a side view along a length 206 of body 102, and FIG. 13 is a side view along a width 208 of body 102. Detail views of the manually actuatable component 502 included in the example device shown in FIGS. 8-13 are shown in FIGS. 14 and 15. Like-numbered elements shown in FIGS. 8-15 correspond to like-numbered elements shown in FIGS. 1-7 and described above.

The example DBS collection device 100 shown in FIGS. 8-13 includes a body 102 with a top plate 124 and a bottom plate 126 coupled together forming a card-shaped cassette or clamshell device having a length 206, width 208, and thickness 210. In this example, the length 206 is greater than the width 208 and the thickness 210 is at least 4 times less than the width 208. For example, the width 208 may be approximately 55 mm, the length 206 may be approximately 78 mm, and the thickness 210 may be approximately 12 mm. The body 102 may include any suitable material. As one non-limiting example, the top plate 124 and the bottom plate 126 may include a plastic material and may be coupled together via one or more interlocking components positioned adjacent to an outer perimeter of the body 102. Though not shown in the figures, DBS collection device 100 may include a desiccant in the interior cavity 112 of body 102 for drying out a blood sample during shipping, for example.

Body 102 of the DBS collection device 100 shown in FIGS. 8-13 defines an inlet 104 of a passage 106 extending from an exterior of the body 102 to an outlet 110 in an interior cavity 112 of the body 102. In this example, inlet 104 is formed in a raised region 802 of body 102 at top surface 836. The raised region 802 extends a non-zero distance above the top surface 836. The inlet 104 is positioned at the center of a top surface of the raised region 802 and edges of the top surface of the raised region 802 are rounded, curving downwardly from the inlet 104 to form an inverted C-shaped protrusion above top surface 836. The raised region 802 is included to assist a user in placing a lanced finger over the inlet 104 in order to transfer blood into the passage 106.

In this example, the passage 106 includes a capillary tube 822 having a predetermined length and diameter/gauge sized to hold a predetermined amount of blood, e.g., 3 µL of blood. For example, the capillary tube 822 may have a length of approximately 11.5 mm, an inner diameter of approximately 0.577 mm, and an outer diameter of approximately 1.35 mm. A portion of capillary tube 822 is mounted within a tubular orifice 804 formed within the raised portion 802 beneath the inlet 104. The tubular orifice 804 may be sized to receive and fixedly hold capillary tube 822 thereby forming passage 106. In particular, the capillary tube 822 mounted inside of the tubular orifice 804 may form the passage 106 extending from the inlet 104 to the outlet 110.

The DBS collection device 100 shown in FIGS. 8-13 includes a cylindrically-shaped platform 114 coupled to the body 102 within the interior cavity 112. Platform 114 is positioned directly beneath outlet 110 of passage 106 so that a central axis of the passage 106 corresponds to a central axis of the cylindrically-shaped platform 114. Platform 114 is configured to hold a specifically-sized absorbent disk 116 in a fixed position on a circular region 118 on a top surface of platform 114. The top surface of the platform 114 includes absorbent disk mounting components 1402 (FIGS. 14 and 15) configured to position and hold an absorbent disk 116 in a fixed position on the top surface of the platform 114. In this example, the mounting components 1402 include small cylindrical protrusions or posts on the top surface of the platform 114 and are positioned around a circumference of the absorbent disk 116 to hold the absorbent disk 116 in place with an interference fit. For example, as shown in FIGS. 14 and 15, the top surface of the platform 114 may include three protrusions 1402 on the top surface 1503 of platform 114 positioned around the circumference of the absorbent disk 116 and spaced on the top surface 1503 such that the distance between adjacent pairs of protrusions on the top surface 1503 is substantially the same for each adjacent pair of protrusions (e.g., the protrusions are evenly spaced). Though FIGS. 14 and 15 show cylindrical protrusions 1402 positioned around the absorbent disk 116 to hold the absorbent disk 116 in place, it should be understood that any number and any suitable type of mounting components 1402 may be used to position and hold the absorbent disk 116 in a fixed position on the top surface 1503 of the platform 114 without departing from the scope of the present disclosure.

As shown in FIGS. 14 and 15, the platform 114 defines a cylindrical aperture 1551 positioned beneath the absorbent disk 116 and extending through the center of the platform 114 along a central axis of the platform 114. Additionally, as shown in FIGS. 14 and 15, the top surface 1503 of platform 114 may include smaller protrusions or posts 1510 positioned between the larger protrusions 1402. The smaller protrusions 1510 may extend above the top surface 1503 of the platform 114 by a distance which is less than the distance that the larger protrusions 1402 extend above the top surface 1503 of the platform 114. A bottom surface of the absorbent disk 116 may be supported by the smaller protrusions 1510 so that the absorbent disk is positioned a non-zero distance above the top surface 1503 of the platform 114, thereby permitting air to flow beneath the absorbent disk 116 and through the cylindrical aperture 1551 to accelerate drying of the absorbent disk 116 after a blood sample is transferred thereto.

The DBS collection device 100 shown in FIGS. 8-13 includes a manually actuatable component 502 coupled to platform 114 such that actuation of the manually actuatable component 502 causes the platform 114 to move toward the outlet 110 in a direction along the central axis of the passage 106 until the absorbent disk 116 on the platform 114 is in physical contact with the outlet 110 (as shown in FIGS. 9, 14, and 15 and discussed below). In this example, manually actuatable component 502 is adjustable between a first position and a second position relative to the body 102, wherein, in the first position when an absorbent disk 116 is mounted in a fixed position on the circular region 118 on the platform 114, the outlet 110 is not in physical contact with the absorbent disk 116 and, in the second position when an absorbent disk 116 is mounted in the fixed position on the platform 114, the outlet 110 is in physical contact with the absorbent disk 116.

The example manually actuatable component 502 shown in FIGS. 8-15 includes a slidable button 871 (FIG. 8) on an exterior surface of body 102. The button 871 is coupled to platform 114 via a coupling element 1502 (FIG. 15) which is affixed to the button 871 adjacent to a top portion of the button 871 and coupled to a bottom portion of the platform 114. In some embodiments, coupling element 1502 may be disposed between the base of platform 114 and the backside of the button 817. The coupling element 1502 is shaped and sized to fit within an elongated aperture 950 in a wall of the body 102 so that the coupling element 1502 is moveable within the elongated aperture 950 in a direction parallel to a central axis of the passage 106. Additionally, a tab 902 (FIGS. 9 and 14) is coupled to a back side of button 871 (at a position below platform 114) and is sized and shaped to be slidable between opposing tracks 904 mounted in the interior cavity 112 below the platform 114 and oriented in directions parallel to the central axis of the passage 106. A bottom back portion of the platform 114 also includes a tab 906 which is sized to fit between the tracks 904 when the manually actuatable component 502 is moved in a downward direction away from the outlet 110.

In this example, platform 114 is biased via a spring 806 such that, in the absence of actuation or force applied to manually actuatable component 502, the platform 114 is maintained in a position wherein the absorbent disk 116 does not touch the outlet 110. Spring 806 extends from an interior surface of raised region 802 to at least partially wrap around the outer surface of the platform 114 and interfaces with the top surface of coupling element 1502 so that the spring 806 exerts a downward force on the platform 114, thereby maintaining a non-zero distance between the absorbent disk 116 and the outlet 110 in absence of actuation of the manually actuatable component 502. For example, a user may place a lanced finger on the raised portion 802 so that a blood sample is transferred into the passage 106 while the manually actuatable component 502 is not actuated and thus that the spring 806 biases the outlet 110 away from the absorbent disk 116. Once a volume of blood is transferred into the passage 106, the user may apply an upward force to the button 871 in a direction parallel to the central axis of the passage 106 and towards the inlet 104 until the absorbent disk 116 physically touches the outlet 110. The user may then maintain the applied force on the button 871 so that the contact between the absorbent disk 116 and the outlet 110 is maintained to facilitate transfer of blood from the passage 106 to the absorbent disk 116. Once a sufficient amount of blood is transferred from the passage 106 to the absorbent disk 116, the user may release the force applied to the button 871 so that the outlet 110 is again separated from the absorbent disk 116.

DBS collection device 100 shown in FIGS. 8-13 additionally includes a window 702 which allows a user to visually inspect a transfer of blood from the passage 106 to the absorbent disk 116 while engaging the manually actuatable component 502. In this example, the window 702 includes a transparent portion of a wall of the body 102 at a corner 880 of the body 102 adjacent to the inlet 104. For example, the window 702 may be composed of a substantially transparent plastic material which is inserted into a cutout in the wall of the body 102 adjacent to corner 880. The transparent window 702 may be mounted in the cutout in the wall of body 102 such that the transparent window 702 may be unsnapped and removed at a lab, for example. After removal of the window 702, the component comprising the platform 114 and the manually actuatable component 502 may be removed from body 102 so that the absorbent disk 116 can be accessed for testing. This removable component comprising the platform 114 and the manually actuatable component 502 may provide a laboratory technician with a conveniently-sized part for handling, and, in some examples, may include bar code information or other indicia which may be inspected or scanned at the lab.

DBS collection device 100 shown in FIGS. 8-13 also includes a lancet system 418 (FIG. 9). Lancet system 418 includes a lancet 420 having a needle 422 extending from a body of the lancet, a lancet actuation component 426, a lancet depth adjustment component 424, and a lancet port 462 formed as an opening in an outer wall of body 102. Lancet 420 is slidably mounted in the interior cavity 112 of body 102 and is in communication with the lancet actuation component 426 such that when the lancet actuation component 426 is actuated, a portion of the needle 422 is projected out through the lancet port 462.

In the non-limiting example shown in FIGS. 8-13, the lancet system 418 includes a biasing spring 458 positioned between a base 951 of lancet 420 and a spring base component 456 mounted within the interior cavity 112 of body 102. The lancet 420 is held in a trigger-ready position within the interior cavity 112 by a latch 454 coupled to the lancet actuation component 426. In the trigger-ready position, the biasing spring 458 is compressed between the lancet 420 and the spring base component 456 to confer a potential energy to the biasing spring 458. This potential energy may be released in response to removal of the latch 454. Actuation of the lancet actuation component 426 may release the latch 454 from the lancet 420 thereby permitting the biasing spring 458 to propel the lancet 420 so that the needle 422 of the lancet 420 protrudes out of the lancet port 462 by a predetermined distance. Actuation of the lancet actuation component 426 by removal of the latch 454 is discussed in further detail below.

In the non-limiting example shown in shown in FIGS. 8-13, the lancet actuation component 426 includes a lever having a fulcrum 812 dividing the lever into a first region 810 and a second region 808. The fulcrum 812 may include a rod 933 (FIG. 9) coupled to an underside of the lancet actuation component 426 in the interior cavity 112. Ends of the rod 933 may be pivotally mounted in supports 937 coupled to an internal wall in the interior cavity 112 of the body 102. The lever may be composed of any suitable material, e.g., plastic, and may have any suitable dimensions. In one example, as shown in FIG. 10, the lever has a width 953 which is at least two times less than a length 955 of the lever. Further, in this example, the width 953 of the lever is greater than a thickness 961 (FIG. 8) of the lever, e.g., the width 953 may be at least 5 times greater than the thickness 961, to form a thin, flat, pivotable actuating component which is at least partially rotatable about the fulcrum 812. In this non-limiting example, a length 957 of the first region 810 is greater than a length 959 of the second region 808. A distal end 870 of the second region 808 has rounded edges so that the outer surface at the distal end 870 of the second region 808 forms a half-circle shape (as shown in FIGS. 8 and 10). An underside of the second region 808 includes a latch 454 at the distal end 870 which engages the lancet 420 to hold the lancet 420 in a trigger-ready position wherein the spring 458 is compressed. Prior to actuation of the lancet actuation component 426 while the latch 454 is engaged with the lancet 420, the first region 810 may be recessed within an aperture 1004 (FIG. 10) in body 102 so that the outer surface of the first region 810 is in substantially the same plane as the outer surface of the body 102 adjacent to the first region 810. The first region 810 is moveable into the interior cavity 112 of the body 102 via aperture 1004. The outer surface of the second region 808 may be positioned above a plane of the outer surface of body 102 adjacent to the second region 808 so that the second region 808 protrudes above a surface of the body 102 as shown in FIG. 12. First region 810 may additionally include a guiding element 1002 (FIG. 10) on the outer surface near a distal end of the first region 810. Guiding element 1002 may include a mark, e.g., a circular mark, or indentation for indicating a location to apply force to actuate the lancet 420.

The lancet 420 is slidably mounted within two opposing tracks 470 coupled to an inner wall of the body 102 in the interior cavity 112 such that the lancet 420 is moveable within the interior cavity 112 between a first position where the lancet needle 422 is fully contained within the interior cavity 112 and a second position where a length of the needle 422 extends outside of the lancet port 462. The length of the portion of the needle 422 projected out of the lancet port 462 may be adjusted via a manual adjustment of the lancet depth adjustment component 424. In this non-limiting example, the lancet depth adjustment component 424 includes a slider positioned on the top surface 836 of body 102. A plurality of raised elements, or treads, is formed on the top surface of the slider. The raised portions on the top surface of the slider may increase the coefficient of friction when a user applies a lateral force to the top surface of the slider to move the slider in a direction parallel to top surface 836. The slider is coupled to a blocking element 450 through an elongated aperture 1211 (FIG. 12) in the top surface 836. For example, a user may apply a lateral force to the slider to move a portion of the blocking element 450 into a path of the top surface 480 of lancet 420 in order to decrease a depth of penetration of the lancet needle 422.

In the non-limiting example of the DBS collection device 100 shown in FIGS. 8-13, the lancet depth adjustment component 424 additionally includes a tab 814 (FIG. 8) coupled to a side of the lancet depth adjustment component 424 near the center of the lancet depth adjustment component 424. The tab 814 may have edges extending downwardly from the top surface 836 that taper to a pointed end. Indicia 440 may be included on an outer surface of body 102 at a position beneath the pointed end of tab 814. The indicia 440 may include markings or labels which indicate different lancet depths corresponding to different positions of the lancet depth adjustment component 424. For example, when the lancet depth adjustment component 424 is in a first position, the pointed end of tab 814 on lancet depth adjustment component 424 may be directly above a first depth marking corresponding to a first length that the lancet needle 422 would protrude out of lancet port 462 upon actuation of the lancet 420; when the lancet depth adjustment component 424 is in a second position, the pointed end of tab 814 on lancet depth adjustment component 424 may be directly above a second depth marking corresponding to a second different length that the lancet needle 422 would protrude out of lancet port 462 upon actuation of the lancet 420.

In the non-limiting example of the DBS collection device 100 shown in FIGS. 8-13, the lancet system 418 is a single-use lancet system such that, after an initial actuation of the lancet 420 which causes the needle 422 to protrude out of the lancet port 462, the needle 422 automatically retracts back into the interior cavity 112 and stays in the interior cavity 112 during subsequent lancet actuation attempts following the initial actuation. For example, in order to actuate the lancet 420, the user may apply a force to the first region 810 of the lancet actuation component 426 in a direction toward the interior cavity 112 of the body 102. Such a force would cause the lever to rotate about the fulcrum 812 so that the latch 454 at the distal end 870 of the second region 808 of the lancet actuation component 426 is disengaged from the lancet 420, thereby permitting the (spring biased) lancet 420 to move toward the lancet port 462 so that a portion of the needle 422 extends out of the lancet port. The latch 454 may be coupled to lancet 420 by a set of hooks on each part (not shown). When DBS collection device 100 is assembled, the lancet 420 may be placed such that it loads compression spring 458 and is then retained in a compressed position by the hook on latch 454. The hook on latch 454 may release the lancet 420 when lancet actuation component 426 is pushed (and the breakable component 452 is broken or yields), and compression spring 458 may then push lancet 420 forward. In this example, the lancet 420 includes two opposing wings 991 (FIG. 9) coupled to opposing sides of the lancet 420 and in contact with opposing tracks 470 when the lancet 420 is launched toward the lancet port 462. The opposing wings 991 each include flared ends 993 which are curved/bent outwardly away from a central axis of the needle 422 adjacent to an end of the lancet 420 opposite from needle 422. After the lancet 420 is launched (via the spring 458) toward the lancet port 462 following disengagement of latch 454, the lancet 420 moves toward the lancet port 462 until the flared ends 993 come into contact with tracks 470. The flared ends 993 may hold the lancet 420 in place. A counter-biasing spring (like the counter-biasing spring 460 of FIG. 2), weaker than compression spring 458, then creates a counter-biasing force when the lancet 420 is launched forward and reaches a "hard stop"; the counter-biasing spring "pushes" the lancet 420 back some small distance until the counter-biasing spring and the compression spring 458 equilibrate. This causes the lancet 420 to retract back into the interior cavity 112 after the needle 422 briefly protrudes from the lancet port 462 so that the tip of the needle 422 does not protrude from the DBS collection device 100. In this example, after actuation and retraction of the lancet 420, the location of the lancet 420 in the interior cavity 112 is such that the needle 422 is fully contained within the interior cavity 112 but at a location which is different from the location of the lancet 420 in the trigger-ready state. As such, the latch 454 may not engage the lancet 420 after an initial actuation and the lancet 420 may not again be actuated.

Figure 16:
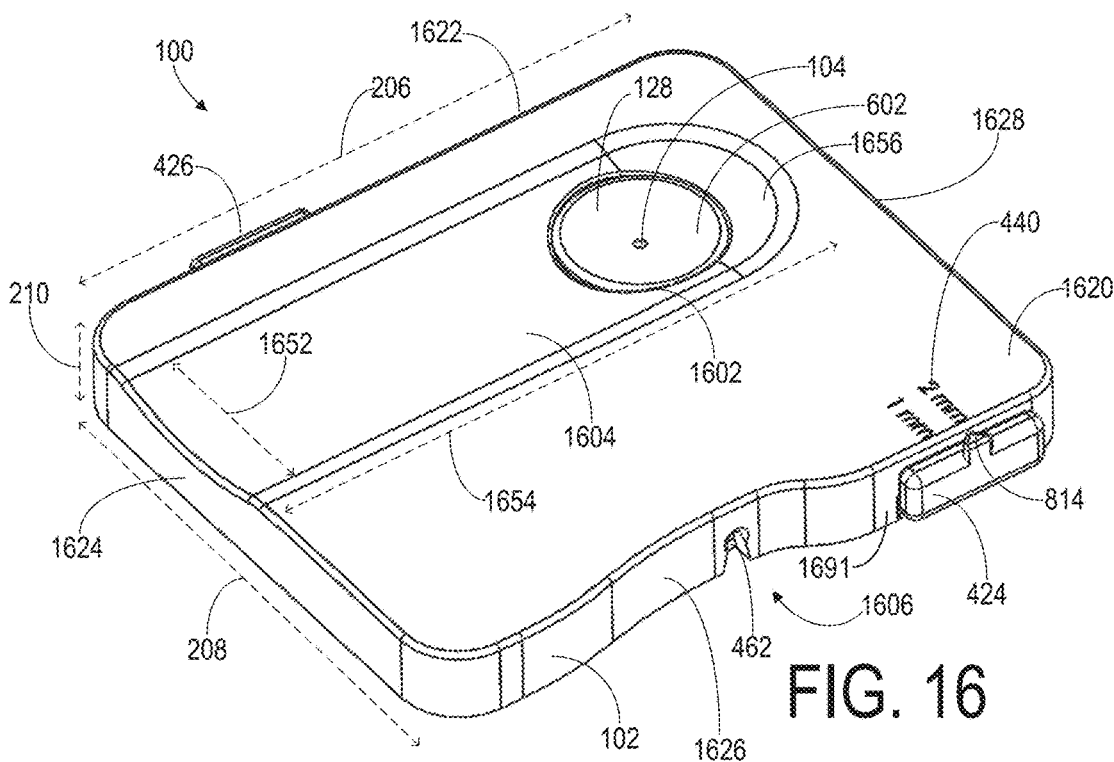
FIG. 16 is a front perspective view of another example of a dried blood spot collection device, in accordance with various embodiments.
Figure 17:
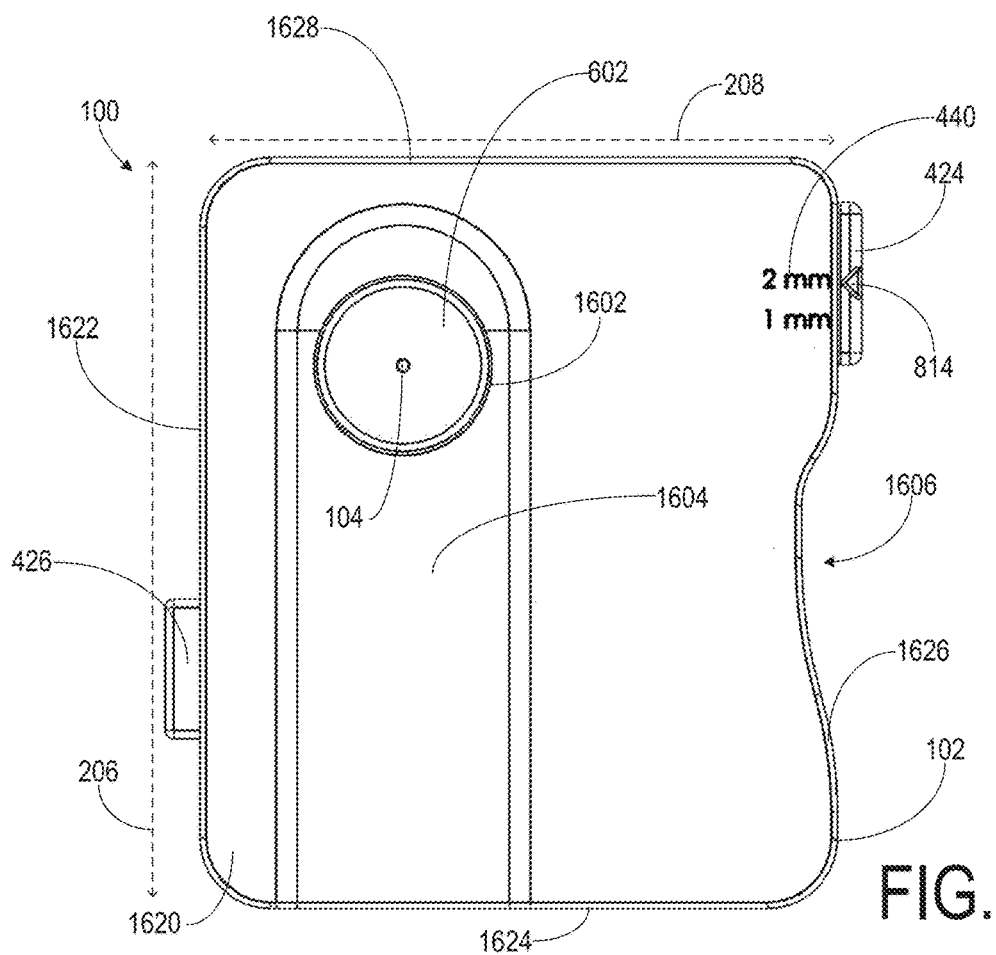
FIG. 17 is a front view of the a dried blood spot collection device shown in FIG. 16, in accordance with various embodiments.
Figure 18:
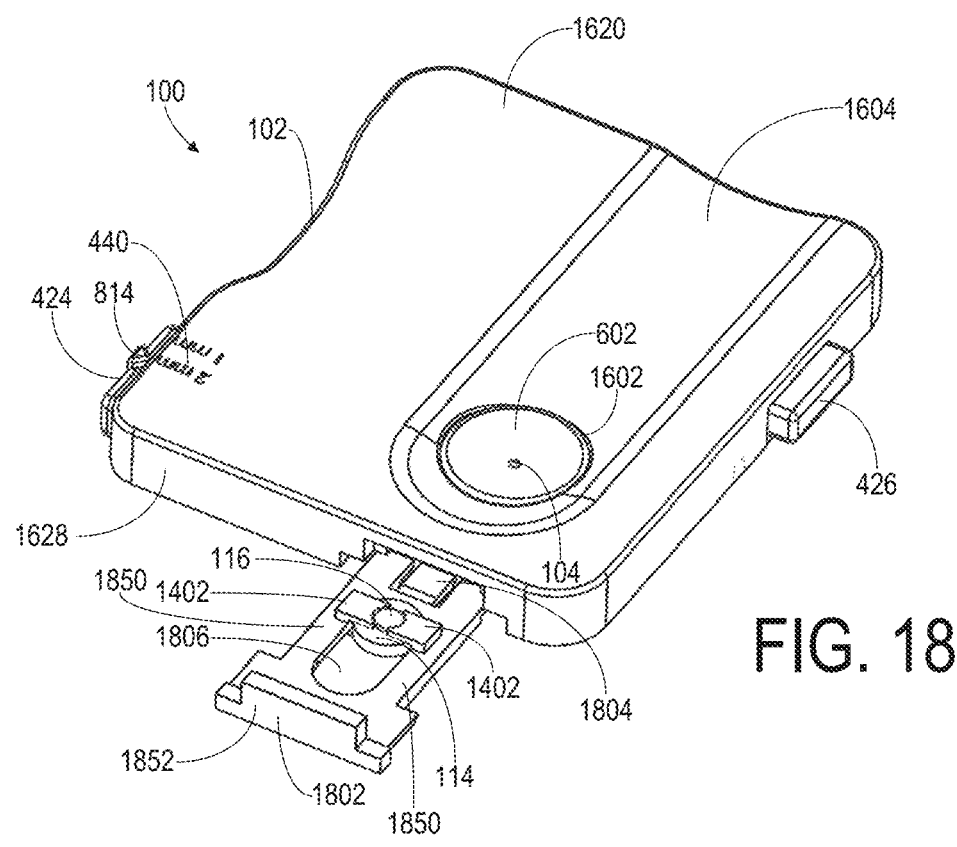
FIG. 18 is another front perspective view of the a dried blood spot collection device shown in FIG. 16, in accordance with various embodiments.
Figure 19:
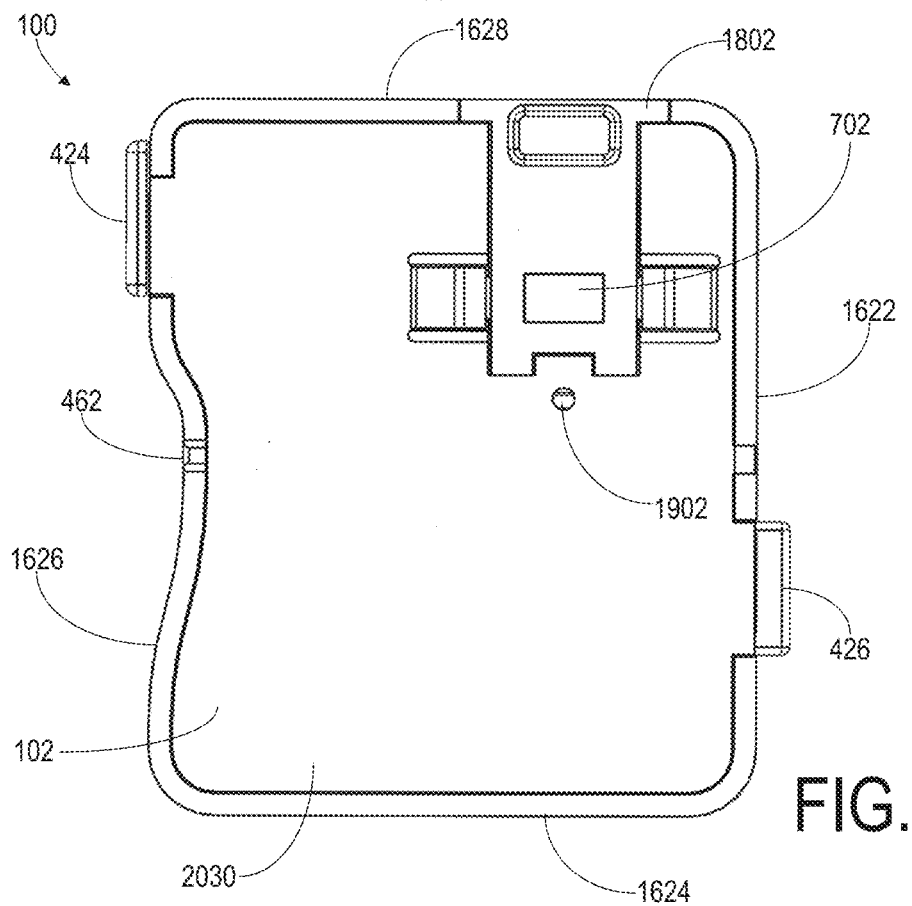
FIG. 19 is a back view of the a dried blood spot collection device shown in FIG. 16, in accordance with various embodiments.
Figure 20:
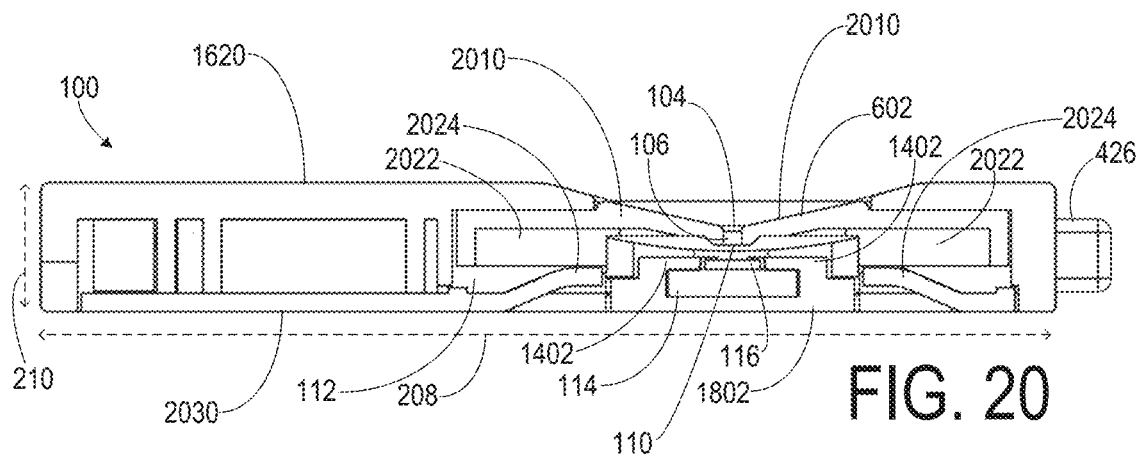
FIG. 20 is a side view of the a dried blood spot collection device shown in FIG. 16, in accordance with various embodiments.
Figure 21:
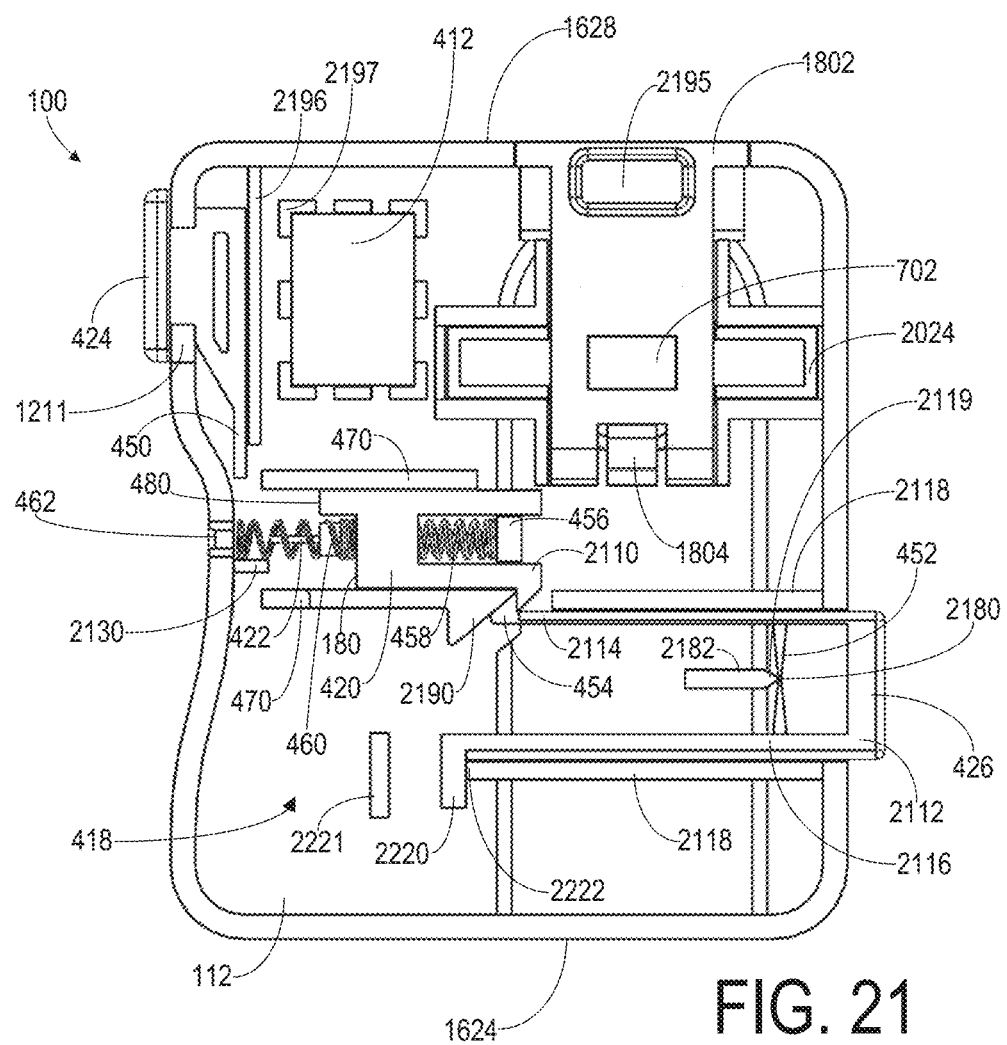
FIG. 21 is a back view of the a dried blood spot collection device shown in FIG. 16 shown with internal components exposed, in accordance with various embodiments.
Figure 22:
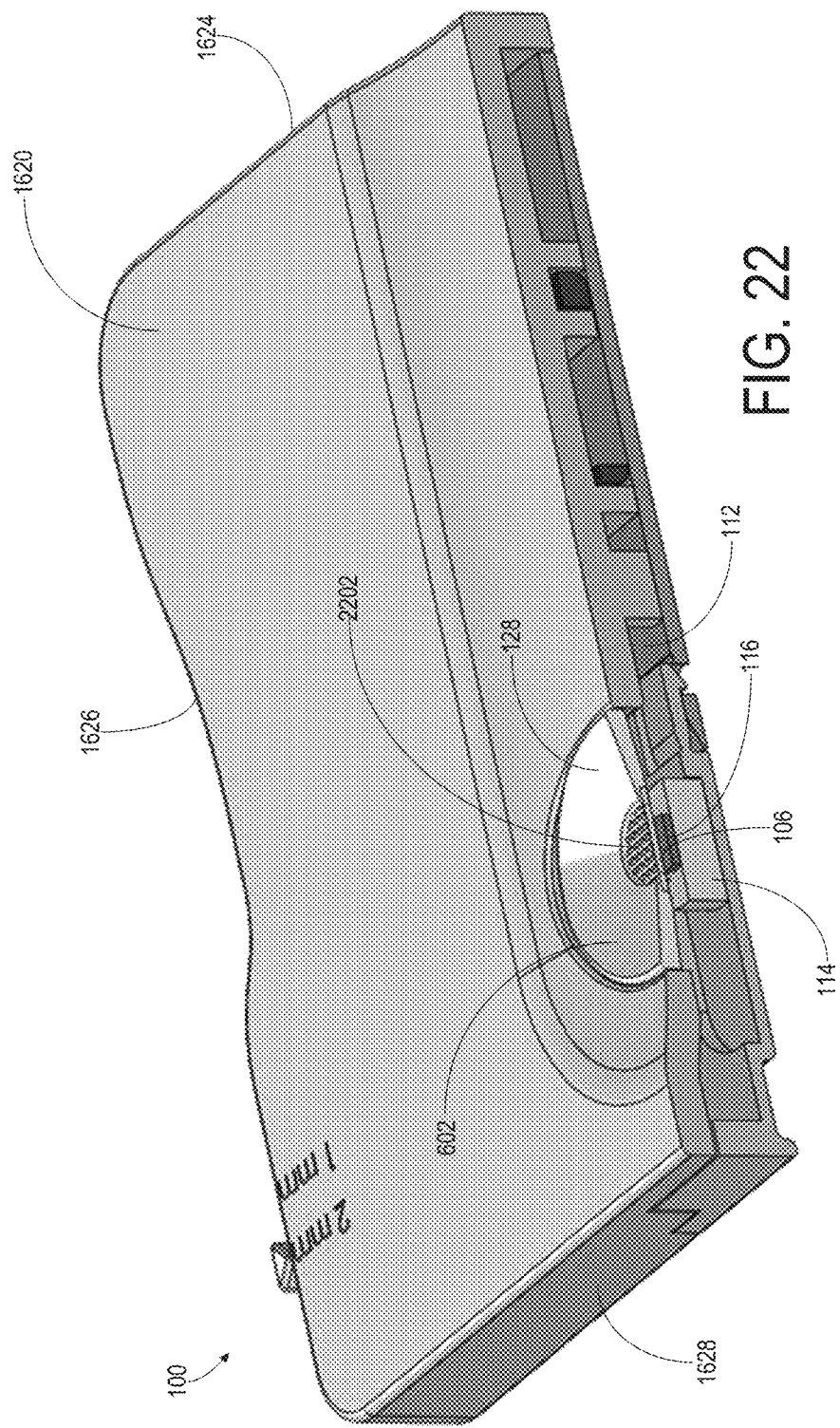
FIG. 22 is a cross-sectional view of another example of a dried blood spot collection device, in accordance with various embodiments.

FIGS. 16-21 show various views of another example embodiment of a DBS collection device 100 having a manually actuatable component 602. In particular, FIG. 16 is a front perspective view of DBS collection device 100, FIG. 17 is a front view of DBS collection device 100, FIG. 18 is another front perspective view of DBS collection device 100, FIG. 19 is a back view of DBS collection device 100, FIG. 20 is a side view of DBS collection device 100, and FIG. 21 is a back view of DBS collection device 100 with internal components exposed. Like-numbered elements shown in FIGS. 16-21 correspond to like-numbered elements shown in FIGS. 1-15 and described above.

The example DBS collection device 100 shown in FIGS. 16-21 includes a body 102 having a length 206, width 208, and thickness 210. In this example, the length 206 is greater than the width 208 and the thickness 210 is at least 4 times the width 208. As a non-limiting example, the length 206 may be approximately 65 mm, the width 208 may be approximately 55 mm, and the thickness 210 may be approximately 6 mm. The body 102 may include any suitable material or combination of materials. As one non-limiting example, the body 102 may be composed of a plurality of plastic components coupled together to form a housing which includes various components, examples of which are described below. One or more contours may be formed in body 102 to provide a user feedback for finger placement while using the DBS collection device 100. In this example, a side 1626 of the body includes an indented region 1606 in which a width of the body 102 in the indented region 1606 is less than the width 208 of the body at sides 1624 and 1628, thereby forming an indented profile when viewed from a top surface 1620. A lancet port 462 is positioned in the indented region 1606 at a location in side 1626 wherein the width of the body 102 is at a minimum. The indented region 1606 may assist a user in holding the body 102 and positioning a finger over lancet port 462.

Body 102 of the DBS collection device 100 shown in FIGS. 16-21 defines an inlet 104 of a passage 106 extending from an exterior of the body 102 to an outlet 110 in an interior cavity 112 of the body 102. In this example, passage 106 includes a capillary passage. However, it should be understood that any suitable passage or orifice may be used without departing from the scope. For example, as shown in FIG. 22 described below, passage 106 may include a screened orifice.

In this example, inlet 104 is formed in a manually actuatable component 602 positioned in an aperture 1602 in the top surface 1620 of the body. The manually actuatable component 602 takes the form of a funnel having inwardly slanted walls 2010 (FIG. 20) which slope inwardly from top surface 1620 toward the interior cavity 112 and terminate at the inlet 104 of passage 106. The top surface 1620 additionally includes a channel 1604 recessed in the top surface 1620 forming an indented contour on an elongated region of the top surface 1620. The channel 1604 includes a recessed region of the top surface 1620 having a width 1652 and a length 1654. The channel 1604 extends from side 1624 toward the opposing side 1628 and terminates in a rounded region 1656 at a position on top surface 1620 offset by a non-zero distance from side 1628. Manually actuatable component 602 is positioned within aperture 1602 in the channel 1604 adjacent to the rounded region 1656. The channel 1604 may assist in guiding finger placement into the funnel and directing blood from a lanced finger positioned in or near the funnel into the inlet 104.

In the example shown in FIGS. 16-21, the passage 106 is formed by walls 2010 (FIG. 20) of the manually actuatable component 602 beneath the inlet 104 and opens into the interior cavity 112 via the outlet 110. The passage 106 may have a predetermined length and predetermined diameter or gauge that are sized to meter the amount of blood delivered to the absorbent disk 116. In this example, DBS collection device 100 includes a disk-shaped platform 114 coupled to the body 102 within the interior cavity 112. The platform 114 is positioned directly beneath outlet 110 of passage 106 so that a central axis of the passage 106 corresponds to a central axis of the platform 114. In this example, the platform 114 includes an absorbent and/or porous material which is in physical contact with a bottom surface of the (primary) absorbent disk 116. The secondary absorbent or porous material may be a porous polymer material, absorbent paper, or any other suitable absorbent or porous material which functions to absorb excess blood that is not absorbed by the absorbent disk 116. The secondary absorbent material may have any suitable physical dimensions, properties, or characteristics, e.g., average pore size, porosity, shape, volume, surface area, etc., selected to provide a balance of relative capillary forces between the absorbent disk 116 and the absorbent platform 114 such that blood in excess of a predetermined absorbent disk saturation volume is drawn from the absorbent disk 116 into the secondary absorbent material. For example, an average pore size of the secondary absorbent material may be greater than an average pore size of the absorbent disk 116. Such an approach operates on a self-regulating principle that uses the balance of relative capillary forces between interacting materials to achieve a consistency of blood volume in the absorbent disk 116. The balance may be achieved through careful selection of materials and their capillary properties, for example. In particular, when blood is introduced to the top of absorbent disk 116 via inlet 104, it may wick into the absorbent disk 116 via capillary forces presented by the internal structure of the absorbent disk 116. Excessive amounts of blood, e.g., a larger volume of blood than the absorbent disk 116 is capable of absorbing, may be presented to the top surface of the absorbent disk 116. On its own, the absorbent disk 116 may tend to oversaturate with blood and leave a residue of extra blood on its top surface. However, with the secondary absorbent material present on the other side of the absorbent disk 116, a capillary pressure may be created between the secondary absorbent material and the absorbent disk 116. The secondary absorbent material may have physical properties or characteristics selected to provide a capillary pressure between the absorbent disk 116 and the secondary absorbent material that is too weak, e.g., a capillary pressure which is less than an upper capillary pressure threshold, to wick correctly-saturated blood from the absorbent disk 116 so that the volume of blood in the absorbent disk 116 remains greater than a lower specification limit for testing. Concurrently, the secondary absorbent material may provide a capillary pressure between the absorbent disk 116 and the secondary absorbent material which is strong enough, e.g., a capillary pressure which is greater than a lower capillary pressure threshold, to wick excessive blood from the absorbent disk 116 so that the volume of blood remaining in the absorbent disk 116 is less than an upper specification limit for testing. As a non-limiting example, the absorbent disk 116 may include a 3 mm diameter GE DMPK-A paper dot (manufactured by GE Healthcare BioSciences Corp. of Piscataway, N.J.) resting on top of an absorbent material comprising a 7 mm diameter, 1.6 mm thick POREX disc (manufactured by Porex Corp., Fairburn, Ga.). For example, the disc may include a POREX X-4899 Polyethylene sheet with a pore size of approximately 50 to 90 microns.

As a non-limiting example, the platform 114 may include an absorbent and/or porous disk composed of an absorbent and/or porous material having a diameter greater than the diameter of the absorbent disk 116. In some examples, the diameter of the platform 114 may be at least twice as large as the diameter of the absorbent disk 116. However, in other examples, the secondary absorbent material of the platform 114 may have substantially the same size, e.g., may have substantially the same diameter, as the absorbent disk 116. In still other examples, the secondary absorbent material of the platform 114 may be smaller than, e.g., have a diameter less than, the absorbent disk 116. For example, a diameter of the secondary absorbent material may be approximately the same as the diameter of the passage 106 but may be less than the diameter of the absorbent disk 116. Further, in some examples, the secondary absorbent material may have a different shape than the absorbent disk 116.

In the illustrated embodiment, the platform 114 is mounted in a releasable cartridge 1802 (FIG. 18) having a front outwardly facing end 1852 coupled to two opposing tracks 1850 which are slidably mounted in the internal cavity 112 of body 102. The tracks 1850 form an oval-shaped aperture 1806 in a bottom side of the releasable cartridge 1802. In particular, when viewed from top surface 1620, the two opposing ends of aperture 1806 have half-circle shapes which open into the center of the aperture 1806 (as shown in FIG. 18). The platform 114 may be mounted in the inner half-circle shaped end of aperture 1806. For example, a diameter of the inner half-circle shaped end of aperture 1806 may be approximately the same as the diameter of the platform 114. Absorbent disk mounting components 1402 are coupled to the tracks 1850 to hold the absorbent disk 116 in place at the center of the top surface of platform 114, e.g., a center of the absorbent disk 116 may be directly aligned with a center of the platform 114. The mounting components 1402 may include opposing tabs mounted on opposing tracks 1850 and extending over the top surface of platform 114 to terminate at opposing concave arc-shaped ends which interface with opposing sides of the absorbent disk 116 to hold the absorbent disk 116 in a fixed position on the top surface of platform 114 via an interference fit.

The releasable cartridge 1802 is slidable between a first position, wherein the cartridge 1802 is inside internal cavity 112 and the front end 1852 is substantially flush with the outer surface of side 1628, and a second position (shown in FIG. 18) wherein the releasable cartridge 1802 extends outside of the interior cavity 112. In the first position, releasable cartridge 1802 positions the absorbent disk 116 mounted on platform 114 directly below the outlet 110 (FIG. 20). The releasable cartridge 1802 may include a locking mechanism 1804, e.g., a tab or snap feature, which interfaces with an internal component to hold the releasable cartridge 1802 in the first position. In order to unlock the releasable cartridge 1802, a user may insert a suitable tool into an aperture 1902 (shown in FIG. 19) positioned in a bottom surface 2030 of body 102 to move or unsnap the locking mechanism 1804 so that the releasable cartridge 1802 is free to be slid out of the interior cavity 112 into the second position. For example, a laboratory technician may unlock the releasable cartridge 1802 via aperture 1902 in order to remove releasable cartridge 1802 from DBS collection device 100 to gain access to the absorbent disk 116 for processing. In some examples, a traction element 2195, e.g., an indentation or the like, may be included on a bottom portion of releasable cartridge 1802 to assist a user in gripping the cartridge 1802 to remove the cartridge 1802. In some examples, the releasable cartridge 1802 may include indicia, e.g., markings, labels, bar codes, etc. which may be inspected or scanned by a laboratory technician.

In the example shown in FIGS. 16-21, while the releasable cartridge 1802 is locked in the first position within interior cavity 112, the platform 114 remains in a fixed position whereas the passage 106 is moveable relative to body 102 via actuation of manually actuatable component 602. The manually actuatable component 602 includes opposing internal braces 2022 (FIG. 20) extending from opposing sides of the funnel in the interior cavity 112 that interface with spring components 2024. For example, spring components 2024 may include cantilever springs mounted to a bottom interior surface of body 102, e.g., the spring components 2024 may be formed with a pass core when the bottom interior surface is molded. The spring components 2024 exert an upward force to the opposing internal braces 2022 so that, in the absence of actuation or force applied to manually actuatable component 602, the manually-actuatable component 602 is maintained in a lifted position wherein the outlet 110 does not physically touch the absorbent disk 116.

For example, when a lanced finger is placed onto manually actuatable component 602 above passage 106 and used to apply a downward force to the manually actuatable component 602 in a direction toward platform 114 along the central axis of the passage 106, the passage 106 is moved downward toward platform 114 until the outlet 110 is in physical contact with absorbent disk 116 mounted on platform 114. In this position, the inlet 104 may provide initial capillary action to help draw the blood to the absorbent disk 116 while the outlet 110 is in contact with the absorbent disk 116. Once a blood sample has been transferred to the absorbent disk 116, the lanced finger may be released from the manually actuatable component 602 thereby separating the absorbent disk 116 and the outlet 110.

The DBS collection device 100 shown in FIGS. 16-21 additionally includes a window 702 (FIG. 19) which, in this example, is positioned in the bottom surface 2030 of body 102 directly below the disk-shaped platform 114, thereby allowing a user to visually inspect a bottom surface of platform 114. In some embodiments, the platform 114 may be transparent to allow a visual inspection of blood absorbed by the platform 114. The window 702 may be composed of a substantially transparent plastic material which is inserted into a cutout in the bottom surface 2030 of body 102. The DBS collection device 100 shown in FIGS. 16-21 additionally includes a desiccant pad 412 mounted to an interior wall in interior cavity 112 via one or more mounting components 2197 (FIG. 21) to assist in drying blood transferred to the absorbent disk 116 and to maintain a reduced humidity level inside the DBS collection device 100. As discussed above, desiccant pad 412 may include any suitable hygroscopic substance that induces or sustains a state of dryness.

DBS collection device 100 shown in FIGS. 16-21 includes a lancet system 418 (FIG. 21). Lancet system 418 includes a lancet 420 having a needle 422 extending from a body of the lancet 420, a lancet actuation component 426, a lancet depth adjustment component 424, and a lancet port 462 formed as an opening in an outer wall of body 102. Lancet 420 is slidably mounted in the interior cavity 112 of body 102 and in communication with the lancet actuation component 426 such that when the lancet actuation component 426 is actuated, a portion of the needle 422 is projected out through the lancet port 462. In this non-limiting example, the lancet system 418 includes a biasing spring 458 positioned between a base portion of lancet 420 and a base component 456 affixed within the interior cavity 112 of body 102.

The lancet 420 is held in a trigger-ready position within the interior cavity 112 by a latch 454 (FIG. 21) coupled to the lancet actuation component 426. Latch 454 interfaces with a tab 2110 extending from a bottom portion of the lancet 420. In the trigger-ready position, the biasing spring 458 is compressed between the lancet 420 and the base component 456 to confer a potential energy to the spring which may be released in response to disengagement of the latch 454 with tab 2110. Actuation of the lancet actuation component 426 may release the latch 454 from tab 2110, thereby permitting the biasing spring 458 to propel the lancet 420 so that the needle 422 of the lancet 420 protrudes out of the lancet port 462 by a predetermined distance.

In this non-limiting example, the lancet actuation component 426 includes a button 2112 having a first extension 2114 and a second extension 2116 extending therefrom into the interior cavity 112 of the body 102. The first extension 2114 and the second extension 2116 are parallel and slidably mounted within opposing tracks 2118. A distal end of the first extension 2114 includes latch 454 which interfaces with tab 2110 on lancet 420 to hold the lancet 420 in a trigger-ready position. A distal end of the second extension 2116 includes a tab 2220 perpendicular to the second extension 2116. Tab 2220 is positioned between an end 2222 of one of the tracks 2118 in the interior cavity 112 and a blocking component 2221 mounted in the interior cavity. When the lancet 420 is in the trigger-ready position with the latch 454 engaging the tab 2110, the tab 2220 may physically touch end 2222 so that the tab 2220 cannot move in an outward direction from the internal cavity 112 beyond end 2222. When actuated, the tab 2220 may move toward blocking component 2221 and blocking component 2221 may prevent movement of the tab 2220 beyond the blocking component 2221, thereby limiting a range of movement of the lancet actuation component 426.

The lancet 420 is slidably mounted within two opposing tracks 470 mounted on an inner wall of the body 102 in the interior cavity 112 such that the lancet 420 is moveable within the interior cavity 112 between a first position where the needle 422 is fully contained within the interior cavity 112 and a second position where a length of the needle 422 extends outside of the lancet port 462. The length of the portion of the needle 422 projected out of the lancet port 462 may be adjusted via a manual adjustment of the lancet depth adjustment component 424. In this non-limiting example, the lancet depth adjustment component 424 includes a slider positioned on side 1622 of body 102. The slider is coupled to a blocking element 450 (FIG. 21) through an elongated aperture 1211 in the side 1622. The blocking element 450 may be supported by a track 2196 which is parallel to a bottom surface of blocking element 450. For example, a user may apply a lateral force to the slider to move a portion of the blocking element 450 into a path of the top surface 480 of lancet 420 in order to decrease a depth of penetration of the needle 422.

In the non-limiting example DBS collection device 100 shown in FIGS. 16-21, the lancet depth adjustment component 424 additionally includes a tab 814 (FIG. 16) coupled to a side 1691 of the lancet depth adjustment component 424 near the center of the lancet depth adjustment component 424. The tab 814 may have edges extending toward indicia 440 included on the top surface 1620. Indicia 440 may be included on an outer surface of body 102 at a position beneath the pointed end of tab 814. The indicia 440 may include markings or labels which indicate a different lancet depths corresponding to different positions of the lancet depth adjustment component 424.

In the non-limiting example DBS collection device 100 shown in FIGS. 16-21, the lancet system 418 is a single-use lancet system, such that, after an initial actuation of the lancet 420 which causes the needle 422 to protrude out of the lancet port 462, the needle 422 automatically retracts back into the interior cavity 112 and stays in the interior cavity 112 during subsequent lancet actuation attempts following the initial actuation. In this example, the lancet system 418 includes a counter-biasing spring 460 (FIG. 21) which interfaces with the lancet 420 to retract the needle 422 after actuation of the lancet 420. For example, a first end of the counter-biasing spring 460 may be in contact with top surface 180 of lancet 420 and a second end of the counter-biasing spring 460, opposite the first end, may be in contact with an inner surface of body 102 adjacent to the lancet port 462 and may be held in position by a blocking element 2130 coupled to the inner surface adjacent to the lancet port 462. The counter-biasing spring 460 may supply a counter-biasing force to the lancet 420 in a direction along a central axis of the needle 422 away from the lancet port 462. The counter-biasing force provided by the counter-biasing spring 460 may be less than the biasing force provided by the biasing spring 458. For example, the spring constant of the counter-biasing spring 460 relative to the spring constant of the biasing spring 458 may be such that when the counter-biasing spring 460 and the biasing spring 458 are in equilibrium, the lancet 420 is at a position in the interior cavity 112 where the needle 422 of the lancet 420 does not protrude out of the lancet port 462.

In the example shown in FIGS. 16-21, the lancet actuation component 426 includes a breakable component 452 (FIG. 21) which breaks or degrades following an initial actuation of the lancet 420 so that the lancet actuation component 426 is no longer functional following the initial actuation. In this example, the breakable component 452 is coupled perpendicularly between the first extension 2114 and the second extension 2116 in the internal cavity 112. A width of the breakable component 452 tapers from the first and second extensions to a minimum width at the center 2180 of the breakable component 452 thereby forming an hour-glass shape. A spike 2182 is mounted within the interior cavity 112 between the first extension 2114 and the second extension 2116 and beneath the thin center 2180 of the breakable component 452. In this example, spike 2182 has a pointed end 2119 which is positioned directly beneath the thin center 2180 of the breakable component 452 when the lancet 420 is in the trigger-ready position with the latch 454 engaged with the tab 2110. In order to actuate the lancet 420, the user may apply an inward force to button 2112 to cause the first and second extensions 2114 and 2116 to move toward the lancet port 462 in a direction parallel to a central axis of the needle 422. This movement may cause the thin center 2180 of the breakable component 452 to break as it is pushed into the pointed end 2119 of spike 2182. In particular, when the breakable component 452 breaks, the lancet 420 cannot retract to a spring-loaded configuration; even if the lancet 420 were able to return to its original position, no component would retain it in place. During initial actuation, the inward force applied to the lancet actuation component 426 when a user presses the button 2112 would cause the latch 454 to be forced against a sloping component 2190 away from tab 2110 so that the latch disengages the tab 2110, thereby permitting the compressed spring 458 to launch the lancet 420 toward the lancet port 462 so that the needle 422 protrudes a predetermined distance outside of the lancet port 462. The counter-biasing spring 460 may then exert a counter force to retract the lancet 420 back into the interior cavity 112 so that the needle 422 is again fully contained in the interior cavity 112.

FIG. 22 is a cross-sectional view of another example DBS collection device 100. The example DBS collection device 100 shown in FIG. 22 is similar to the example device shown in FIGS. 16-21 and described above, except that the passage 106 includes a screened orifice 2202. The screened orifice 2202 may include any suitable material, e.g., plastic stainless steel, etc., and may be formed in any suitable way. For example, the screen of the screened orifice 2202 may be a woven mesh or a photo-etched blank that can be stamped at predetermined dimensions. Screened orifice 2202 may include a plurality of passages, where each passage in the plurality of passages includes an inlet opening to an exterior of body 102 and an outlet opening into the interior cavity 112 of the body 102. As in the example device shown in FIGS. 16-21, in the example of FIG. 22, the screened orifice 2202 is maintained disconnected from the absorbent disk 116 until a downward force is applied to the manually actuatable component 602. Such an approach may provide an increased surface wicking area and allow for more room for error in placement of a lanced finger at the inlet while maintaining no skin contact with the absorbent disk 116 during sample transfer to the disk.

Figure 23:
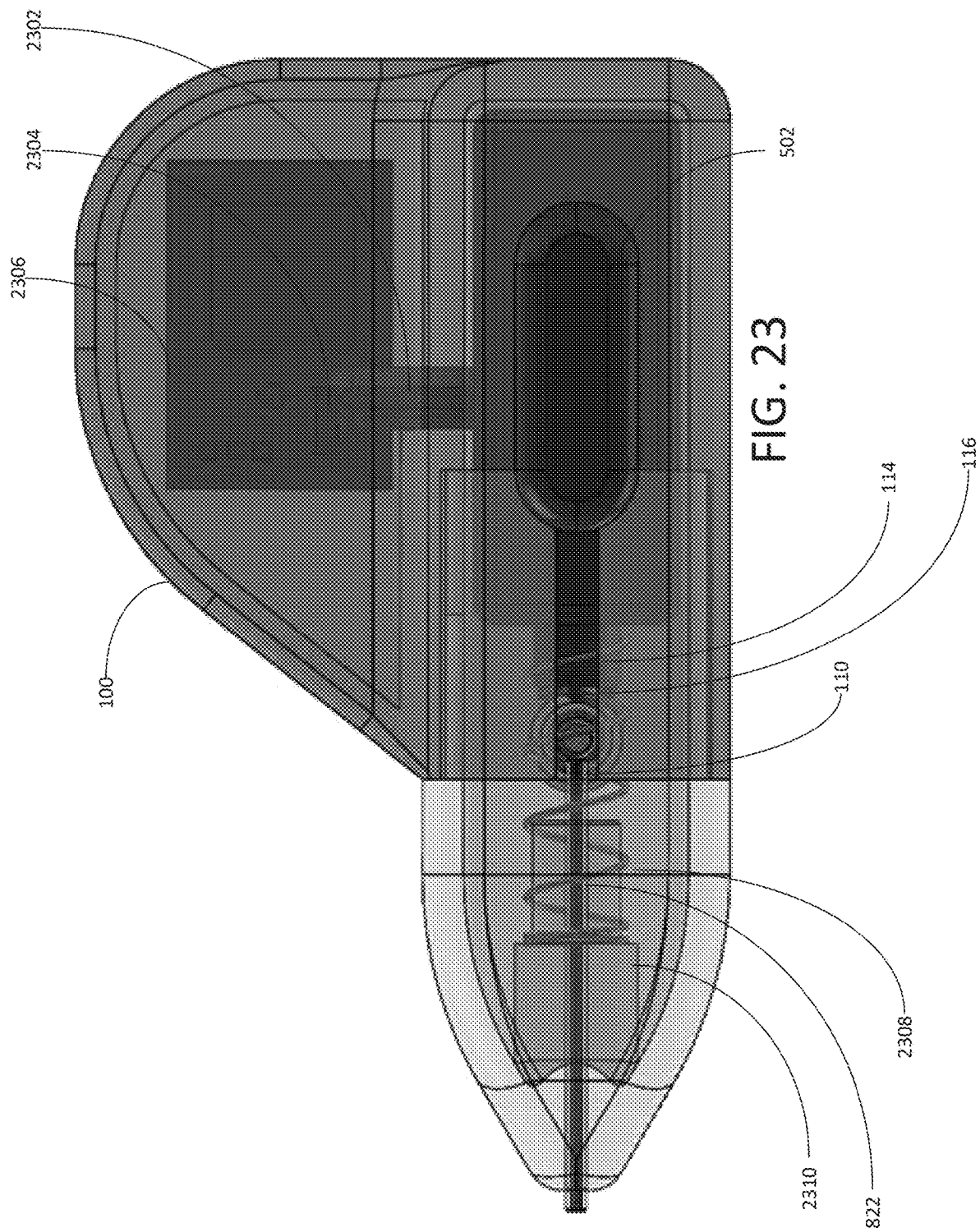
FIG. 23 illustrates another example of a dried blood spot collection device, in accordance with various embodiments.

FIG. 23 illustrates another example of a dried blood spot collection device, in accordance with various embodiments. The DBS collection device 100 shown in FIG. 23 includes a manually actuatable component 502 that includes or is coupled to the platform 114 such that the manually actuatable component 502 causes the platform 114 to move toward the outlet 110 until the absorbent disk 116 on the platform 114 is in physical contact with the outlet 110. In this example, the manually actuatable component further includes an extension 2302 that engages a switch 2304 on a printed circuit assembly 2306. The printed circuit assembly 2306 may be populated such that triggering of the switch 2304 by the extension 2302 captures the time and date at which the sample was taken.

In the illustrated example, the DBS collection device 100 includes a compression spring 2308 that traverses the space between the platform 114 and a stopper 2310 that surrounds the capillary tube 822. The compression spring 2308 returns the manually actuatable component 502 to its original position and disengages the outlet 110 from the absorbent disk 116.

It is to be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated may be performed in the sequence illustrated, in other sequences, in parallel, or in some cases omitted. Likewise, the order of the above-described processes may be changed.

The subject matter of the present disclosure includes all novel and nonobvious combinations and subcombinations of the various processes, systems and configurations, and other features, functions, acts, and/or properties disclosed herein, as well as any and all equivalents thereof. For example, embodiments of manually actuable components in which a platform moves toward an outlet of a passage may be combined with embodiments in which a passage moves toward a platform such that both mechanisms are included in a single device.

The invention claimed is:

1. A dried blood spot collection device, comprising:
a body defining an elongate capillary passage extending from an outer surface of the body to an interior cavity of the body, the capillary passage having a longitudinal central axis, an inlet end, and an outlet end, the capillary passage configured to hold an amount of blood sufficient to at least saturate an absorbent disk and configured to move the blood from the outer surface of the body to the interior cavity of the body for application to the absorber disk maintained within the interior cavity of the body;
a platform coupled to the body within the interior cavity, the platform having a surface for holding the absorbent disk in a fixed position on a region of the platform;
a manually actuatable component mounted in the body, the manually actuatable component adjustable up and down along the longitudinal central axis of the capillary passage between a first position and a second position relative to the body, wherein:
in the first position, when an absorbent disk is mounted in the fixed position on the platform, the outlet end of the capillary passage is not in physical contact with the absorbent disk,
in the second position, when an absorbent disk is mounted in the fixed position on the platform, the outlet end of the capillary passage is in physical contact with the absorbent disk to permit the absorbent disk to absorb blood from the capillary passage, and
the longitudinal central axis of the capillary passage is normal to the surface of the platform in both the first position and the second position.

2. The device of claim 1, wherein the absorbent disk comprises a filter paper disk.

3. The device of claim 2, wherein the filter paper disk has a diameter of approximately 6 millimeters.

4. The device of claim 1, wherein the manually actuatable component is spring-biased to remain in the first position when the manually actuatable component is not actuated.

5. The device of claim 1, further comprising a desiccant mounted in the interior cavity of the body.

6. The device of claim 1, wherein the manually actuatable component is coupled to the platform such that actuation of the manually actuatable component causes the platform to move toward the capillary passage in a direction along the longitudinal central axis of the capillary passage.

7. The device of claim 1, wherein the manually actuatable component comprises a region of the body adjacent to and including the capillary passage such that actuation of the manually actuatable component causes the capillary passage to move toward the platform.

8. The device of claim 1, wherein the platform comprises an absorbent material.

9. The device of claim 8, wherein the secondary absorbent material comprises an absorbent and/or porous disk.

10. The device of claim 8, wherein the absorbent material is configured to balance relative capillary forces between the absorbent disk and the absorbent material such that blood in excess of a predetermined absorbent disk saturation volume is drawn from the absorbent disk into the secondary absorbent material.

11. The device of claim 8, wherein an average pore size of the secondary absorbent material is greater than an average pore size of the absorbent disk.

12. The device of claim 8, wherein the absorbent material is configured to provide:
a capillary pressure between the absorbent disk and the secondary absorbent material, where the capillary pressure is lower than an upper capillary pressure threshold to wick correctly-saturated blood from the absorbent disk so that the volume of blood in the absorbent disk remains greater than a lower specification limit, and where the capillary pressure is greater than a lower capillary threshold so that the volume of blood remaining in the absorbent disk is less than an upper specification limit.

13. The device of claim 1, further comprising a printed circuit assembly and a switch operably coupled thereto, wherein triggering of the switch causes the printed circuit assembly to capture a time and/or date.

14. The device of claim 13, wherein the manually actuatable component further includes an extension that engages the switch.

15. The device of claim 2, wherein the filter paper disk has a diameter of approximately 3 millimeters.

16. The device of claim 2, wherein the manually actuatable component is spring-biased to remain in the first position when the manually actuatable component is not actuated.

17. The device of claim 3, wherein the manually actuatable component is spring-biased to remain in the first position when the manually actuatable component is not actuated.

18. The device of claim 4, wherein the manually actuatable component is spring-biased to remain in the first position when the manually actuatable component is not actuated.

19. A method of making a dried blood spot collection using a device comprising:
a body defining an elongate capillary passage extending from an outer surface of the body to an interior cavity of the body, the capillary passage having a longitudinal central axis, an inlet end, and an outlet end, the capillary passage configured to hold an amount of blood sufficient to at least saturate an absorbent disk and configured to move the blood from the outer surface of the body to the interior of the body for application to the absorbent disk maintained within the interior cavity of the body;

a platform coupled to the body within the interior cavity, the platform having a surface for holding the absorbent disk in a fixed position on a region of the platform;

a manually actuatable component mounted in the body, the manually actuatable component adjustable up and down along the longitudinal central axis of the capillary passage between a first position and a second position relative to the body, wherein:

in the first position, when an absorbent disk is mounted in the fixed position on the platform, the outlet end of the capillary passage is not in physical contact with the absorbent disk, in the second position, when an absorbent disk is mounted in the fixed position on the platform, the outlet end of the capillary passage is in physical contact with the absorbent disk, the longitudinal central axis of the capillary passage is normal to the surface of the platform in both the first position and the second position;

the method comprising:
introducing blood into the capillary passage; and
actuating the manually actuable component to cause the platform to move from a first position in which the absorbent disk is not in physical contact with the outlet end of the capillary passage to a second position in which the absorbent disk is in physical contact with the outlet end of the capillary passage to absorb blood from the capillary passage.

20. The method of claim 19, wherein the absorbent disk comprises a filter paper disk.

21. The method of claim 20, wherein the filter paper disk has a diameter of approximately 3 millimeters.

22. The method of claim 20, wherein the filter paper disk has a diameter of approximately 6 millimeters.

23. The device of claim 19, wherein the manually actuatable component is spring-biased to remain in the first position when the manually actuatable component is not actuated.

24. The device of claim 1, wherein the manually actuatable component is configured to be in the first position when blood is introduced into the capillary passage, prior to physical contact of the capillary passage with the absorbent disk.

* * * * *